(12) United States Patent
Amselem et al.

(10) Patent No.: US 10,688,122 B2
(45) Date of Patent: Jun. 23, 2020

(54) THIOL AND DISULFIDE-CONTAINING AGENTS FOR INCREASING MEIBOMIAN GLAND LIPID SECRETION

(71) Applicant: Azura Ophthalmics Ltd., Tel Aviv (IL)

(72) Inventors: Shimon Amselem, Rehovot (IL); Yair Alster, Tel Aviv (IL); Doron Friedman, Carme-Yosef (IL); Omer Rafaeli, Udim (IL)

(73) Assignee: AZURA OPHTHALMICS LTD., Tel Aviv (IL)

( * ) Notice: Subject to any disclaimer, the term of this patent is extended or adjusted under 35 U.S.C. 154(b) by 0 days.

(21) Appl. No.: 15/279,301

(22) Filed: Sep. 28, 2016

(65) Prior Publication Data

US 2017/0087179 A1 Mar. 30, 2017

Related U.S. Application Data

(60) Provisional application No. 62/233,941, filed on Sep. 28, 2015, provisional application No. 62/233,906, filed on Sep. 28, 2015.

(51) Int. Cl.
| | |
|---|---|
| *A61K 33/04* | (2006.01) |
| *A61K 47/44* | (2017.01) |
| *A61K 47/06* | (2006.01) |
| *A61K 31/19* | (2006.01) |
| *A61K 9/00* | (2006.01) |

(Continued)

(52) U.S. Cl.
CPC ............ *A61K 33/04* (2013.01); *A61K 9/0048* (2013.01); *A61K 31/095* (2013.01); *A61K 31/19* (2013.01); *A61K 31/198* (2013.01); *A61K 31/20* (2013.01); *A61K 31/325* (2013.01); *A61K 31/401* (2013.01); *A61K 31/575* (2013.01);
(Continued)

(58) Field of Classification Search
None
See application file for complete search history.

(56) References Cited

U.S. PATENT DOCUMENTS

| | | | |
|---|---|---|---|
| 3,236,730 A | | 2/1966 | Galin |
| 6,153,607 A | * | 11/2000 | Pflugfelder .......... A61K 9/0048 |
| | | | 514/177 |

(Continued)

FOREIGN PATENT DOCUMENTS

| | | |
|---|---|---|
| CN | 101612161 A | 12/2009 |
| EP | 0930072 A1 | 7/1999 |

(Continued)

OTHER PUBLICATIONS

Seifert et al. "Immunocytochemical and ultrastructure evaluation of the distribution of nervous tissue and neuropeptides in meibomian gland", Graefe's Arch Clin Exp Ophthalmol (1996), 234: 648-656.*

(Continued)

*Primary Examiner* — Isis A Ghali
(74) *Attorney, Agent, or Firm* — Wilson Sonsini Goodrich & Rosati

(57) ABSTRACT

Described herein are compositions and methods for the increasing the quantity of lipids secreted from meibomian glands. Such compositions and methods are useful for the treatment of meibomian gland dysfunction and disorders resulting therefrom.

11 Claims, 8 Drawing Sheets

(51) Int. Cl.
*A61K 31/095* (2006.01)
*A61K 31/198* (2006.01)
*A61K 31/20* (2006.01)
*A61K 31/325* (2006.01)
*A61K 31/401* (2006.01)
*A61K 31/575* (2006.01)
*A61K 31/683* (2006.01)
*A61K 45/06* (2006.01)

(52) U.S. Cl.
CPC ............ *A61K 31/683* (2013.01); *A61K 45/06* (2013.01); *A61K 47/06* (2013.01); *A61K 47/44* (2013.01)

(56) References Cited

U.S. PATENT DOCUMENTS

| | | |
|---|---|---|
| 6,348,508 B1 | 2/2002 | Denick, Jr. et al. |
| 7,288,259 B2 | 10/2007 | Sanders et al. |
| 8,420,699 B1 | 4/2013 | Dubow |
| 8,449,928 B2 | 5/2013 | Gilbard et al. |
| 8,455,016 B2 | 6/2013 | Maskin |
| 2004/0171561 A1 | 9/2004 | Popp |
| 2004/0192647 A1 | 9/2004 | Babizhayev |
| 2005/0124690 A1 | 6/2005 | Yoon et al. |
| 2005/0197614 A1 | 9/2005 | Pritchard et al. |
| 2006/0188471 A1 | 8/2006 | Podolsky et al. |
| 2007/0166402 A1 | 7/2007 | Friedlaender et al. |
| 2007/0269537 A1 | 11/2007 | Gupta |
| 2008/0103376 A1 | 5/2008 | Felder |
| 2009/0214676 A1 | 8/2009 | Gao et al. |
| 2009/0238810 A1 | 9/2009 | Nyunt |
| 2010/0034870 A1 | 2/2010 | Sim et al. |
| 2010/0204317 A1 | 8/2010 | Hunt et al. |
| 2010/0256552 A1 | 10/2010 | Korb et al. |
| 2010/0285155 A1 | 11/2010 | Gilbard et al. |
| 2011/0022010 A1 | 1/2011 | Grenon et al. |
| 2011/0059925 A1 | 3/2011 | Donnenfeld |
| 2011/0104206 A1 | 5/2011 | Nanduri et al. |
| 2011/0124725 A1 | 5/2011 | Maskin |
| 2011/0130729 A1 | 6/2011 | Korb et al. |
| 2011/0137214 A1 | 6/2011 | Korb et al. |
| 2011/0294897 A1 | 12/2011 | Aberg et al. |
| 2012/0016275 A1 | 1/2012 | Korb et al. |
| 2012/0028929 A1 | 2/2012 | Power et al. |
| 2012/0093876 A1 | 4/2012 | Ousler, III et al. |
| 2012/0128763 A1 | 5/2012 | Maskin |
| 2012/0190661 A1 | 7/2012 | Trogden et al. |
| 2012/0226156 A1 | 9/2012 | Grenon et al. |
| 2012/0264681 A1 | 10/2012 | Braiman-Wiksman et al. |
| 2012/0288575 A1 | 11/2012 | Gilbard et al. |
| 2013/0053733 A1 | 2/2013 | Korb et al. |
| 2013/0131171 A1 | 5/2013 | Maskin |
| 2013/0184242 A1 | 7/2013 | Eini et al. |
| 2013/0224272 A1 | 8/2013 | Gao et al. |
| 2013/0274214 A1 | 10/2013 | Brubaker |
| 2013/0280340 A1 | 10/2013 | Dobbie |
| 2013/0281390 A1 | 10/2013 | Brubaker |
| 2013/0331768 A1 | 12/2013 | Nichamin |
| 2013/0344128 A1 | 12/2013 | Gao et al. |
| 2013/0345185 A1 | 12/2013 | Mitra et al. |
| 2014/0005171 A1 | 1/2014 | Aukunuru et al. |
| 2014/0058340 A1 | 2/2014 | Guillon et al. |
| 2014/0142055 A1 | 5/2014 | Hosseini et al. |
| 2014/0142668 A1 | 5/2014 | Guillon et al. |
| 2014/0154333 A1 | 6/2014 | Moloney |
| 2015/0265565 A1 | 9/2015 | O'Haimhirgin |
| 2016/0106775 A1 | 4/2016 | Alster et al. |

FOREIGN PATENT DOCUMENTS

| | | | |
|---|---|---|---|
| EP | 1621191 A1 | 2/2006 | |
| EP | 1915998 A1 | 4/2008 | |
| EP | 2633852 A1 | 9/2013 | |
| WO | WO-9611686 A1 | 4/1996 | |
| WO | WO-9724116 A2 | 7/1997 | |
| WO | WO-03035076 A1 | 5/2003 | |
| WO | WO-03050190 A2 | 6/2003 | |
| WO | WO-2007070463 A2 | 6/2007 | |
| WO | WO-2007133703 A2 | 11/2007 | |
| WO | WO-2008027069 A1 | 3/2008 | |
| WO | WO-2008068866 A1 * | 6/2008 | ............ A61K 31/16 |
| WO | WO-2008106228 A2 | 9/2008 | |
| WO | WO-2010006117 A2 | 1/2010 | |
| WO | WO-2012092320 A2 | 7/2012 | |
| WO | WO-2012161112 A1 | 11/2012 | |
| WO | WO-2013003731 A2 | 1/2013 | |
| WO | WO 2015017316 A2 * | 2/2015 | ............ A61K 31/00 |
| WO | WO-2015022546 A1 | 2/2015 | |
| WO | WO-2015169728 A1 | 11/2015 | |
| WO | WO-2017055924 A2 | 4/2017 | |
| WO | WO-2017178892 A2 | 10/2017 | |
| WO | WO-2017182885 A2 | 10/2017 | |

OTHER PUBLICATIONS

Nederfors et al. "Effects of the antihypertensive drug captopril on human salivary secretion rate and composition", European Journal of Oral Sciences, vol. 103, Issue 6, Dec. 1995.*

Millar et al. "The effect of dietary and pharmacological manipulation of lipid production in the Meibomian and Harderian glands of the rabbit" . (Year: 2002).*

Nagymihalyi et al. "The influence of eyelid temperature on the delivery of Meibomian oil", Experimental eye research, 78, 367-370. (Year: 2004).*

Driver et al. "Meibomian Gland Dysfunction", Survey of Ophthalmology; vol. 40, No. 5, Mar.-Apr. 1996 (Year: 1996).*

Geerling et al. "The International Workshop on Meibomian gland Dysfunction: Report of the Subcommittee on Management and Treatment of Meibomian Gland Dysfunction", Inventigative Ophthamology & Visual Science, Special Issue, 2011, vol. 52, No. 4. (Year: 2011).*

U.S. Appl. No. 15/269,833 Office Action dated Jan. 11, 2017.

Akyol-Salman et al. Efficacy of topical N-acetylcysteine in the treatment of meibomian gland dysfunction. J Ocul Pharmacol Ther 26(4):329-333 (2010).

Barrault et al. Immortalized sebocytes can spontaneously differentiate into a sebaceous-like phenotype when cultured as a 3D epithelium. Exp Dermatol 21:299-319 (2012).

Chew et al. An instrument for quantifying meibomian lipid on the lid margin: the Meibometer. Curr Eye Res 12(3):247-254 (1993).

Co-pending U.S. Appl. No. 15/269,833, filed Sep. 19, 2016.

Heiligenhaus et al. Therapy of dry eye disorders [Therapie von Benetzungsstorungen]. Klin Monatsbl Augenheilkd 204:162-168 (1994).

Knop et al. The International Workshop on Meibomian Gland Dysfunction: Report of the Subcommittee on Anatomy, Physiology, and Pathophysiology of the Meibomian Gland. IOVS 52(4):1938-1978 (2011).

Koenig et al. Organic Sulfur Derivatives. V.2 Preparation and Properties of Some Long-Chain Mercapto Acids and Related Compounds. J Org Chem 23:1525-1530 (1958).

PCT/IB2015/02164 International Search Report and Written Opinion dated Mar. 29, 2016.

Qiao et al. Emerging treatment options for meibomian gland dysfunction. Clinical Ophthalmology 7:1797-1803 (2013).

U.S. Appl. No. 14/732,622 Office Action dated Nov. 19, 2015.

Butovich et al. Human tear film and meibum. Very long chain wax esters and (O-acyl)-omega-hydroxy fatty acids of meibum. J Lipid Res 50(12):2471-2485 (2009).

Nichols. The International Workshop on Meibomian Gland Dysfunction: Introduction. Invest Ophthalmol Vis Sci 52(4):1917-1921 (2011).

PCT/IB2015/02164 International Preliminary Report on Patentability dated May 4, 2017.

PCT/US2016/01510 International Search Report and Written Opinion dated May 24, 2017.

U.S. Appl. No. 15/269,833 Office Action dated Aug. 7, 2017.

(56) References Cited

OTHER PUBLICATIONS

Co-pending U.S. Appl. No. 16/019,253, filed Jun. 26, 2018.
PCT/IB2016/01510 International Preliminary Report on Patentability dated Apr. 12, 2018.
Driver et al. Meibomian Gland Dysfunction. Survey of Ophthalmology 40(5):343-367 (1996).
U.S. Appl. No. 16/019,253 Office Action dated May 16, 2019.
Wong et al. Selenium (Selsun) in the Treatment of Marginal Blepharitis. AMA Arch Ophthalmol 55(2):246-253 (1956).
Nelson et al. The International Workshop on Meibomian Gland-Dysfunction: Report of the Definition and Classification Subcommittee. Invest Ophthalmol Vis Sci. 52(4):1930-1937 (2011).

* cited by examiner

THIOL AND DISULFIDE-CONTAINING AGENTS FOR INCREASING MEIBOMIAN GLAND LIPID SECRETION

CROSS REFERENCE

This application claims the benefit of U.S. Provisional Application No. 62/233,906, filed Sep. 28, 2015, and U.S. Provisional Application No. 62/233,941, filed Sep. 28, 2015, both of which are incorporated by reference herein in their entirety.

BACKGROUND OF THE INVENTION

Meibomian glands are glands arranged vertically within the eyelid near the lashes. The force of an eyelid blink causes oil to be excreted onto the posterior lid margin. The oil is the "staying power" of the tears that helps prevent rapid tear evaporation. In a patient with Meibomian gland dysfunction (MGD), vision is affected because there is too much or too little oil in the tear film.

The meibomian glands are large sebaceous glands located in the eyelids, and unlike skin, are unassociated with hair. The meibomian glands produce the lipid layer of the tear film that protects it against evaporation of the aqueous phase. The meibomian gland orifice is located on the epithelial side of the lid margin, and is only a few hundred microns from the mucosal side. The glands are located on both upper and lower eyelids, with higher amounts of the glands on the upper eyelid. A single meibomian gland is composed of clusters of secretory acini that are arranged circularly around a long central duct and connected to it by short ductules. The terminal part of the central duct is lined by an ingrowth of the epidermis that covers the free lid margin and forms a short excretory duct that opens as an orifice at the posterior part of the lid margin just anterior to the mucocutaneous junction near the inner lid border. The oily secretion composed of lipids is synthesized within the secretory acini. The lipid secretion is a liquid at near body temperature and is delivered to the skin of the lid margin as a clear fluid, called "meibum." It forms shallow reservoirs on the upper and lower lid margins, and consists of a complex mixture of cholesterol, wax, cholesteryl esters, phospholipids, with small amounts of triglycerides, triacylglycerols, and hydrocarbons. The separate meibomian glands are arranged in parallel, and in a single row throughout the length of the tarsal plates in the upper and lower lids. The extent of the glands corresponds roughly to the dimensions of the tarsal plates.

The eyelid margin is the source of physiologically important lipid secretion, meibum. The eyelid meibomian gland secretions form the outer layer of the tear film. Functions which have been attributed to this tear film lipid layer are: (1) a lubricant facilitating the movement of the eyelids during a blink, (2) a barrier preventing evaporation of the aqueous tear fluid, and (3) a barrier to the entry of microorganisms and organic matter such as pollen.

The moving eyelids spread meibum across the ocular surface and mix it with aqueous tears (AT), which are produced by lacrimal glands. Mixing and spreading of meibum and AT result in a near-continuous structure called tear film (TF), which covers the entire ocular surface and serves multiple purposes, including protective, lubricatory, nutritional, and antimicrobial, among others. TF was also linked to visual acuity because it provides a smoother ocular surface which improves the optical properties of the eye. However, TF is not homogeneous, which is not surprising considering that lipids do not easily form aqueous solutions and tend to separate by forming a clearly hydrophobic lipid-enriched sub-phase. A classical view on the TF structure presumes a three-layer organization of TF. As lipids are, typically, less dense than water, they accumulate on the surface of the aqueous sub-phase thus forming a lipid-enriched outer-most layer of TF (also called tear film lipid layer, or TFLL). Beneath the TFLL is a much more hydrophilic aqueous layer enriched with water-soluble proteins, carbohydrates, salts, and other more or less hydrophilic compounds. The closest to the corneal epithelium is believed to be a relatively hydrophilic mucin-enriched glycocalyx layer, which is formed primarily of membrane-bound mucins. By using interferometry, the depth of TFLL was estimated to be ~40-90 nanometers, while the aqueous layer was found to be much thicker at about 4 micrometers. It is important to realize that all three layers are soft and dynamic structures, where changes occur as a result of numerous simultaneously manifesting factors, e.g. mechanical movements of the eyelids, continuous secretion of meibum, aqueous tears and mucins, and AT evaporation and drainage through nasal ducts. If the eye is forced to stay open without blinking, the human TF quickly deteriorates, thins, and breaks—a phenomenon known as tear break-up.

The tear break-up time (TBUT) for humans is measured in seconds. It has long been considered an important and objective diagnostic parameter in evaluating the health of the ocular surface. TBUT is widely used in ophthalmic practice to diagnose dry eye—a multifactorial condition (or disease) whose onset and progress is linked to the deterioration of TF in general, and TFLL in particular. When the break-up occurs, the cornea becomes exposed to air, causing a discomfort to the patient. The incomplete coverage of the ocular surface with TF also increases the chances of damage to the corneal epithelium cells because of excessive dehydration, abrasions, irritation, inflammation, infections, etc. Another cause of the TF instability are meibomian glands incapable of secreting enough meibum of the necessary quality, e.g. because of MGD associated with meibomian gland inflammation and/or obstruction.

Lipids produced by the meibomian glands are the main component of the superficial lipid layer of the tear film that protects it against evaporation of the aqueous phase and is believed also to stabilize the tear film by lowering surface tension. Alterations of the lipid phase more frequently point to MGD than alterations in isolated aqueous phase, as reported in a study by Heiligenhaus et al. (Heiligenhaus et al., Therapie. von Benetzungsstörungen. Klin. Monatsbl. Augenheilkd., 1994, Vol. 204, pages 162-168) where it was observed that a lipid deficiency occurred in 76.7% of dry eye patients compared with only 11.1% of those with isolated alterations of the aqueous phase. Hence, meibum lipids are essential for the maintenance of ocular surface health and integrity.

Lipids are the major components of meibum (also known as "meibomian gland secretions"). The biochemical composition of meibum is extremely complex and very different from that of sebum. Lipids are universally recognized as major components of human and animal meibum. In humans, more than 90 different proteins have been identified in meibomian gland secretions. A large number of investigators have attempted to characterize the meibum, and there has been a large range of amounts of lipids recovered by investigators (Table 1), the likely cause being the use of different collection and analysis techniques.

TABLE 1

Type and Amount of Each Lipid Present in the Meibum.

| Lipid | Polarity | Amount |
|---|---|---|
| Free Fatty Acids | Non-Polar | 0.0-10.4% |
| Wax Esters | Non-Polar | 28.0-68.0% |
| Cholesterol Esters | Non-Polar | 0.0-39.0% |
| Diesters | Non-Polar | 2.3-17.6% |
| Free sterols | Non-Polar | Trace-30.0% |
| Monoglycerides | Non-Polar | Trace-2.6% |
| Diglycerides | Non-Polar | Trace-3.3% |
| Triglycerides | Non-Polar | Trace-9.0% |
| Fatty Acid Amides | Non-Polar | Unknown |
| Hydrocarbons | Non-Polar | Trace-7.5% |
| Phospholipids | Polar | 0.0-14.8% |
| Sphingolipids | Polar | Unknown |
| ω-Hydroxy Fatty Acids | Polar | Unknown |

In subjects without MGD, the meibum lipid is a pool of clear oil. In MGD, the quantity, quality and composition of the secreted material is altered. Thus, MGD is characterized by lipid deficiency. Further, in MGD, the quality of expressed lipid varies in appearance from a clear fluid, to a viscous fluid containing particulate matter and densely opaque, toothpaste-like material. The meibomian orifices may exhibit elevations above surface level of the lid, which is referred to as plugging or pouting, and is due to obstruction of the terminal ducts and extrusion of a meibum lipids of increased viscosity.

Lipid deficiency and increased viscosity of meibum are important pathogenic factors in MGD and are observed in majority of cases of obstructive MGD. Therefore it is highly desired to enhance lipogenesis and lipid secretion from the meibomian gland, to overcome lipid deficiency as well as reduce the viscosity of meibum oil composition which allows for dissolution of any obstruction of the meibomian gland.

Highly viscous meibum is mixed with hyperkeratotic cell material, as seen in expressed pathologic human meibum prepared as smears or in impression cytology and in histopathology, as verified by molecular biology and immunohistochemistry. Increased viscosity has also been observed inside the obstructed glands of animal models. It is therefore desirable to soften and liquefy the obstructing lipids in order to open the duct and restore normal flow of excreted lipids.

Meibomian gland dysfunction, or MGD, is a leading contributor of dry eye syndrome, and is often characterized by insufficient lipid delivery, by the meibomian gland, to the surface of the eye. MGD, also termed posterior blepharitis, is the most common form of lid margin disease. In the early stages, patients are often asymptomatic, but if left unmanaged, MGD can cause or exacerbate dry eye symptoms and eyelid inflammation. The oil glands become blocked with thickened secretions. Chronically clogged glands eventually become unable to secrete oil which results in permanent changes in the tear film and dry eyes. Symptoms of MGD include eye dryness, burning sensation, itching, stickiness, watering, sensitivity to light, red eyes, and blurred vision.

MGD is a leading contributor of dry eye syndrome. The occurrence of dry eye syndrome is widespread and affects about 20 million patients in the United States alone. Dry eye syndrome is a disorder of the ocular surface resulting from either inadequate tear production or excessive evaporation of moisture from the surface of the eye. Tears are important to corneal health because the cornea does not contain blood vessels, and relies on tears to supply oxygen and nutrients. Tears and the tear film are composed of lipids, water, and mucus, and disruption of any of these can cause dry eye.

MGD is not synonymous with posterior blepharitis, which describes inflammatory conditions of the posterior lid margin. MGD may cause posterior blepharitis, but MGD may not always be associated with inflammation or posterior blepharitis. Clinical signs of MGD include meibomian gland dropout, altered meibomian gland secretion, and changes in lid morphology.

Obstructive MGD is characterized by all or some of the following: 1) chronic ocular discomfort, 2) anatomic abnormalities around the meibomian gland orifice (which is one or more of the following: vascular engorgement, anterior or posterior displacement of the mucocutaneous junction, irregularity of the lid margin) and 3) obstruction or qualitative or quantitative changes in the glandular secretion (decreased meibum expression by moderate digital pressure).

Currently, standard treatment to MGD is somewhat limited to heating the lids to increase oil production and melt the oil that has solidified in the glands by warm compresses, applying light pressure to the lid margin near the lash line, and manually removing the thickened secretions as well as pharmacological treatments like antibiotics and anti-inflammatory agents. However, these treatments may be frustrating to patients and ophthalmologists. Massage of the eyelid provides only partial and temporary relief of obstruction of the meibomian glands and this could be painful. Conventional approaches for warm compresses apply heat to the outer surface of the eyelid; therefore the heat is frequently of limited effectiveness. The use of topical antibiotics and corticosteroids to suppress the bacterial colonization and inflammation of the eyelid margin associated with MGD has been shown to be effective in the relief of symptoms and the signs of MGD, however, the success of this treatment may have nothing to do with the changed meibum. Antibiotics, particularly the tetracyclines (including doxycycline, tetracycline, and minocycline) and azithromycin are used to suppress bacterial colonization and reduce inflammation of the lid margin; however, drug intolerance and prolonged therapy have limited the clinical application of oral antibiotics.

Lid hygiene is considered the primary treatment for MGD and consists of three components: 1) application of heat, 2) mechanical massage of eyelids and 3) cleansing the eyelid. Eyelid warming procedures improve meibomian gland secretion by melting the pathologically altered meibomian lipids. Warming is achieved by warm compresses or devices. Mechanical lid hygiene includes the use of scrubs, mechanical expression and cleansing with various solutions of the eyelashes and lid margins. Lid margins are optionally also cleansed with hypoallergenic bar soap, dilute infant shampoo or commercial lid scrubs. Physical expression of meibomian glands is performed in a physician's office or is performed by the patient at home. The technique varies from gentle massage of the lids against the eyeball to forceful squeezing of the lids either against each other or between a rigid object on the inner lid surface and a finger, thumb, or rigid object (such as a glass rod, Q-tip, or metal paddle) on the outer lid surface. The rigid object on the inner lid surface protects the eyeball from forces transferred through the eyelid during expression and to offer a stable resistance, to increase the amount of force that is applied to the glands.

Eyelid warming is limited because the warming melts the lipids, but does not address movement of the keratinized material. Further, eyelid warming induces transient visual degradation due to corneal distortion. Mechanical lid hygiene is also limited because the force needed to remove an obstruction can be significant, resulting in significant pain to the patient. The effectiveness of mechanical lid hygiene is limited by the patient's ability to tolerate the associated pain during the procedure. Other treatments for MGD are limited.

Physical opening of meibomian glands obstruction by meibomian gland expression is an acceptable method to improve meibomian gland secretion and dry eye symptoms. In addition probing of the meibomian gland canal has been used to open the obstructed canal. Both methods, expression and probing, are limited, however, by the pain induced by the procedure, the possible physical insult to the gland and canal structures and their short lived effect estimated at days and weeks.

In summary, each of these treatments has a different shortcoming and the treatment of MGD remains challenging. Therefore, methods are needed to improve patient comfort, which will not cause harm to the meibomian glands and canals, that will reduce the dependency on frequent office visits and improve secretion of meibum.

Emerging treatments for MGD include the use of mucolytic and/or keratolytic agents. The goal of mucolytic therapy is to facilitate physiological clearance by optimizing the viscoelasticity of mucus, while keratolytic therapy aims to soften keratin, a major component of the skin.

Acetylcysteine, also known as N-acetylcysteine or N-acetyl-L-cysteine (abbreviated NAC), is a pharmaceutical drug and nutritional supplement used primarily as a mucolytic agent. Acetylcysteine is an acetylated derivative of L-cysteine where an acetyl group is attached to the nitrogen atom, known to have mucolytic, anti-collagenolytic, and anti-oxidant properties. It is used as a cough medicine since it breaks disulfide bonds in mucus and liquefies it, making it easier to cough up. It is also this action of breaking disulfide bonds that makes it useful in thinning the abnormally thick mucus in cystic and pulmonary fibrosis patients. Akyol-Salman et al., (J. Ocul. Pharmacol. Ther., 2010, Vol. 26(4), pages 329-33) evaluated the efficacy of topical N-acetyl-cysteine (NAC) therapy in patients with meibomian gland dysfunction (MGD). Qiao and Yan (Clinical Ophthalmology 2013, Vol. 7, pages 1797-1803) reviewed several emerging treatment options for MGD, including NAC.

Despite the possible treatment options for MGD, it is still difficult to obtain complete relief of signs and symptoms.

SUMMARY OF THE INVENTION

The present invention provides methods for enhancing lipogenesis and/or lipid secretion from the meibomian glands to the eyelid. Without wishing to be bound by any theory or mechanism, it is speculated that enhanced lubrication of the eyelid margin by natural lipids which are the major constituents of the meibum would ameliorate MGD and/or related symptoms.

The present invention is based on the unexpected discovery that include thiol-containing, —SeH containing, and/or disulfide-containing drugs are capable to increase the production of lipids in meibomian glands and/or increase the secretion of lipids from meibomian glands to the eyelid. This capability may be effective in preventing, treating and/or ameliorating certain adverse eyelid conditions, such as MGD.

The present invention provides, in an aspect, a method for increasing lipid secretion from a meibomian gland, comprising topically administering to the eyelid margin of the patient in need thereof an ophthalmic composition comprising an ophthalmically-acceptable carrier and a therapeutically-effective amount of at least one agent which increases lipogenesis in the meibomian gland or increases lipid secretion from the meibomian gland, wherein the agent comprises a sulfhydryl group or a disulfide.

The present invention further provides, in another aspect, a method for treating meibomian gland dysfunction (MGD), comprising topically administering to the eyelid margin of the patient in need thereof an ophthalmic composition comprising an ophthalmically-acceptable carrier and a therapeutically-effective amount of at least one agent, wherein the agent is selected from the group consisting of captopril, Zofenopril, Tiopronin, Penicillamine, Gluthatione, Dithiothreitol, Thiorphan, Cysteamine, Bucillamine, Dimercaprol, 1,1-Ethanedithiol, Dimercaptosuccinic acid, Furan-2-ylmethanethiol, Omapatrilat, Ovothiol A, Pantetheine, Rentiapril, Thiosalicylic acid, Tixocortol, Mycothiol, Coenzyme A, and Coenzyme B, or wherein the agent comprises a disulfide.

The present invention further provides, in another aspect, a method for lowering the melting point of lipids secreted from a meibomian gland, comprising topically administering to the eyelid margin of the patient in need thereof an ophthalmic composition comprising an ophthalmically-acceptable carrier and a therapeutically-effective amount of at least one agent which increases lipogenesis in the meibomian gland or increases lipid secretion from the meibomian gland, wherein the agent comprises a sulfhydryl group or a disulfide The present invention further provides, in another aspect, a method for reducing the viscosity of lipids secreted from a meibomian gland, comprising topically administering to the eyelid margin of the patient in need thereof an ophthalmic composition comprising an ophthalmically-acceptable carrier and a therapeutically-effective amount of at least one agent which increases lipogenesis in the meibomian gland or increases lipid secretion from the meibomian gland, wherein the agent comprises a sulfhydryl group or a disulfide In certain embodiments, the agent comprises thiol group. In certain embodiments, the agent is selected from the group consisting of Captopril, Zofenopril, Tiopronin, Penicillamine, L-Cysteine, Selenocysteine, Gluthatione, Dithiothreitol, Thiorphan, Cysteamine, Bucillamine, Dimercaprol, 1,1-Ethanedithiol, Dimercaptosuccinic acid, Furan-2-ylmethanethiol, Omapatrilat, Ovothiol A, Pantetheine, Rentiapril, Thiosalicylic acid, Tixocortol, Mycothiol, Coenzyme A, and Coenzyme B. In certain embodiments, the agent is selected from the group consisting of Captopril, Zofenopril, Tiopronin, Penicillamine, Gluthatione, Dithiothreitol, Thiorphan, Cysteamine, Bucillamine, Dimercaprol, 1,1-Ethanedithiol, Dimercaptosuccinic acid, Furan-2-ylmethanethiol, Omapatrilat, Ovothiol A, Pantetheine, Rentiapril, Thiosalicylic acid, Tixocortol, Mycothiol, Coenzyme A, and Coenzyme B. Each possibility represents a separate embodiment of the invention.

In certain embodiments, the agent comprises a disulfide bond. In certain embodiments, the agent is selected from the group consisting of disulfiram, Psammaplin A, Dixanthogen, Pantethine, Fursultiamine, Octotiamine, Sulbutiamine, Prosultiamine, Thiram, Lipoic acid, Lenthionine, Ajoene, Allicin, Gemopatrilat, and Sulfanegen. Each possibility represents a separate embodiment of the invention.

In certain embodiments, the ophthalmically-acceptable carrier comprises at least one ophthalmically-acceptable excipient.

In certain embodiments, the methods described above further comprise the step of administering to the patient a keratolytic agent. In certain embodiments, the keratolytic agent is selected from the group consisting of benzoyl peroxide, coal tar, dithranol, salicylic acid, selenium disulfide, alpha-hydroxy acid, urea, boric acid, retinoic acid, lactic acid, sodium thioglycolate or allantoin.

In certain embodiments, the meibomian gland dysfunction is characterized by obstruction of a meibomian gland. In certain embodiments, the topical administration of the agent to the eyelid margin of the patient is repeated until the meibomian gland obstruction is substantially removed. In certain embodiments, the topical administration of the agent to the eyelid margin of the patient is periodically repeated to prevent formation of a meibomian gland obstruction.

BRIEF DESCRIPTION OF THE DRAWINGS

The patent application file contains at least one drawing executed in color. Copies of this patent application with color drawings will be provided by the Office upon request and payment of the necessary fee. An understanding of the features and advantages of the present disclosure will be obtained by reference to the following detailed description that sets forth illustrative embodiments, in which the principles of the disclosure are utilized, and the accompanying drawings of which.

DETAILED DESCRIPTION OF THE INVENTION

Figure 1:
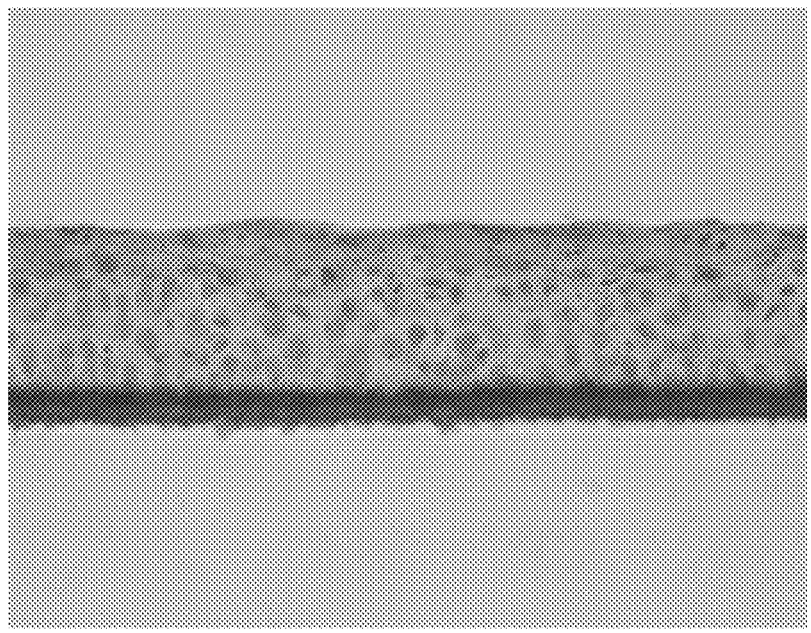
FIG. 1 is an illustration of Oil-red-0 staining in 3D Sebocytes epithelium for the control.

The present invention provides, for the first time, non-hormonal agents useful for enhancing secretion of the meibum lipids in vivo.

More specifically, described herein are methods for enhancing lipogenesis and/or lipid secretion by administering a thiol-containing, —SeH containing, or disulfide-containing agent which increases the production of lipids in meibomian glands, increases the quantity of lipids secreted from meibomian glands, and/or alters the composition of lipids secreted from meibomian glands. The agents described herein include agents for acute therapies, for use, e.g., by a physician or other trained specialist, and agents for chronic therapies, e.g., either by a physician or other trained specialist, or by the patient. Certain lipogenesis and lipid secretion enhancing agents are described herein; further provided herein are methods for preparing a composition comprising lipogenesis and lipid secretion enhancing thiol-containing, —SeH containing, or disulfide-containing agents as well as their use in methods of treatment of patients.

The terms "meibomian gland dysfunction" and "MGD" as interchangeably used herein, refer to chronic, diffuse abnormality of the meibomian glands, that is characterized by terminal duct obstruction or qualitative or quantitative changes in the glandular secretion, or both. MGD may result in alteration of the tear film viscosity, eye irritation symptoms, inflammation, or ocular surface disease. The most prominent aspects of MGD are obstruction of the meibomian gland orifices and terminal ducts and changes in the meibomian gland secretions. MGD also refers to functional abnormalities of the meibomian gland, while "meibomian gland disease," describes a broad range of meibomian gland disorders, that includes neoplasia and congenital disease.

According to the principles of the present invention, thiol-containing, —SeH containing, or disulfide-containing drugs or agents which induce lipogenesis and meibum lipid secretion, can be used, e.g., as treatment for MGD through thiol-mediated lipid over-secretion mechanisms. More according to the principles of the present invention, disulfide containing drugs, like disulfiram, present thiol or sulfhydryl radicals once the disulfide bond is cleaved within the body by enzymes or chemical reactions.

Drug-induced activation of cellular lipogenesis thus represents a new approach for therapeutic treatment of meibomian gland dysfunction through enhanced synthesis of cholesterol and increased production of fatty acids and triglycerides that lead to alterations in composition of the meibum lipids, by decreasing the melting point and viscosity of the meibum lipids, which results in a more fluid appearance of meibum lipids.

The lipogenesis and lipid secretion enhancing thiol-containing, —SeH containing, or disulfide-containing agents described herein are useful either as an acute therapy (e.g., by a trained specialist or physician) or as a chronic therapy (e.g., in the hands of a patient, or alternatively, by a trained specialist or physician). The agents are tested, in certain embodiments, using the assays and methods described herein (e.g., as described in the examples).

Drugs that have thiol groups, or sulfhydryl radicals have previously been reported to cause sebum over-production. Drugs containing thiol groups or sulfhydryl radicals were also reported to cause Pemphigus, a skin disease resembling seborrheic dermatitis, characterized by oily skin. Xanthine oxidoreductase (XOR) is an essential enzyme for milk lipid droplet secretion and it is known to exist in two distinct and interconvertible enzymatic forms, a thiol reduced form (XD) and a thiol oxidized form (XO), which differ in their enzymatic properties and conformations. Mammary tissue and milk fat globule membranes (MFGM) have been shown to contain a thiol oxidase that is capable of converting XD to XO. The association between XOR and the apical plasma membrane is mediated by thiol-dependent processes that involve the formation of disulphide bond cross-links with Butyrophilin protein (the most abundant protein in MFGM also essential for secretion of lipid droplets in mammary gland), ADPH or other membrane proteins, and/or conformational changes in XOR. The levels of expression and the apical membrane localization of XOR are crucial properties of secreting mammary epithelial cells and the membrane association of XOR regulates coupling of cytoplasmic lipid droplets to the apical plasma membrane during lipid secretion.

The present invention provides, in an aspect, a method for increasing lipid secretion from a meibomian gland, comprising topically administering to the eyelid margin of the patient in need thereof an ophthalmic composition comprising an ophthalmically-acceptable carrier and a therapeutically-effective amount of at least one agent which increases lipogenesis in the meibomian gland or increases lipid secretion from the meibomian gland, wherein the agent comprises a sulfhydryl group, —SeH group, or a disulfide.

The present invention provides, in an aspect, a method for increasing lipid secretion from a meibomian gland, comprising topically administering to the eyelid margin of the patient in need thereof an ophthalmic composition comprising an ophthalmically-acceptable carrier and a therapeutically-effective amount of an agent which increases lipogenesis in the meibomian gland or increases lipid secretion from the meibomian gland, wherein the agent comprises a sulfhydryl group, —SeH group, or a disulfide.

The present invention provides, in an aspect, a method for increasing lipid secretion from a meibomian gland, comprising topically administering to the eyelid margin of the patient in need thereof an ophthalmic composition consisting of an ophthalmically-acceptable carrier and a therapeutically-effective amount of an agent which increases lipogenesis in the meibomian gland or increases lipid secretion from the meibomian gland, wherein the agent comprises a sulfhydryl group, —SeH group, or a disulfide.

The present invention provides, in an aspect, a method for increasing lipid secretion from a meibomian gland, comprising topically administering to the eyelid margin of the patient in need thereof an ophthalmic composition consisting of an ophthalmically-acceptable carrier and a therapeutically-effective amount of an agent which increases lipogenesis in the meibomian gland or increases lipid secretion from the meibomian gland, wherein the agent comprises a sulfhydryl group, —SeH group, or a disulfide, and wherein the ophthalmically-acceptable carrier comprises at least one ophthalmically-acceptable excipient.

The present invention provides, in an aspect, a method for increasing lipid secretion from a meibomian gland, comprising topically administering to the eyelid margin of the patient in need thereof an ophthalmic composition consisting of an ophthalmically-acceptable carrier and a therapeutically-effective amount of an agent which increases lipogenesis in the meibomian gland or increases lipid secretion from the meibomian gland, wherein the agent comprises a sulfhydryl group, —SeH group, or a disulfide, and wherein the ophthalmically-acceptable carrier comprises no more than two ophthalmically-acceptable excipients.

The present invention provides, in an aspect, a method for increasing lipid secretion from a meibomian gland, comprising topically administering to the eyelid margin of the patient in need thereof an ophthalmic composition consisting of an ophthalmically-acceptable carrier and a therapeutically-effective amount of an agent which increases lipogenesis in the meibomian gland or increases lipid secretion from the meibomian gland, wherein the agent comprises a sulfhydryl group, —SeH group, or a disulfide, and wherein the ophthalmically-acceptable carrier comprises no more than three ophthalmically-acceptable excipients.

The present invention provides, in an aspect, a method for increasing lipid secretion from a meibomian gland, comprising topically administering to the eyelid margin of the patient in need thereof an ophthalmic composition consisting of an ophthalmically-acceptable carrier and a therapeutically-effective amount of an agent which increases lipogenesis in the meibomian gland or increases lipid secretion from the meibomian gland, wherein the agent comprises a sulfhydryl group, —SeH group, or a disulfide, and wherein the ophthalmically-acceptable carrier comprises no more than four ophthalmically-acceptable excipients.

The present invention further provides, in another aspect, a method for treating meibomian gland dysfunction (MGD), comprising topically administering to the eyelid margin of the patient in need thereof an ophthalmic composition comprising an ophthalmically-acceptable carrier and a therapeutically-effective amount of at least one agent, wherein the agent is selected from the group consisting of Captopril, Zofenopril, Tiopronin, Penicillamine, Gluthatione, Dithiothreitol, Thiorphan, Cysteamine, Bucillamine, Dimercaprol, 1,1-Ethanedithiol, Dimercaptosuccinic acid, Furan-2-ylmethanethiol, Omapatrilat, Ovothiol A, Pantetheine, Rentiapril, Thiosalicylic acid, Tixocortol, Mycothiol, Coenzyme A, and Coenzyme B, or wherein the agent comprises a disulfide.

The present invention further provides, in another aspect, a method for lowering the melting point of lipids secreted from a meibomian gland, comprising topically administering to the eyelid margin of the patient in need thereof an ophthalmic composition comprising an ophthalmically-acceptable carrier and a therapeutically-effective amount of at least one agent which increases lipogenesis in the meibomian gland or increases lipid secretion from the meibomian gland, wherein the agent comprises a sulfhydryl group, —SeH group, or a disulfide The present invention further provides, in another aspect, a method for reducing the viscosity of lipids secreted from a meibomian gland, comprising topically administering to the eyelid margin of the patient in need thereof an ophthalmic composition comprising an ophthalmically-acceptable carrier and a therapeutically-effective amount of at least one agent which increases lipogenesis in the meibomian gland or increases lipid secretion from the meibomian gland, wherein the agent comprises a sulfhydryl group, —SeH group, or a disulfide In certain embodiments, the agent comprises thiol group, or —SeH group. In certain embodiments, the agent is selected from the group consisting of Captopril, Zofenopril, Tiopronin, Penicillamine, L-Cysteine, Selenocysteine, Gluthatione, Dithiothreitol, Thiorphan, Cysteamine, Bucillamine, Dimercaprol, 1,1-Ethanedithiol, Dimercaptosuccinic acid, Furan-2-ylmethanethiol, Omapatrilat, Ovothiol A, Pantetheine, Rentiapril, Thiosalicylic acid, Tixocortol, Mycothiol, Coenzyme A, and Coenzyme B. In certain embodiments, the agent is selected from the group consisting of Captopril, Zofenopril, Tiopronin, Penicillamine, Gluthatione, Dithiothreitol, Thiorphan, Cysteamine, Bucillamine, Dimercaprol, 1,1-Ethanedithiol, Dimercaptosuccinic acid, Furan-2-ylmethanethiol, Omapatrilat, Ovothiol A, Pantetheine, Rentiapril, Thiosalicylic acid, Tixocortol, Mycothiol, Coenzyme A, and Coenzyme B. Each possibility represents a separate embodiment of the invention.

In certain embodiments, the agent is a —SH or —SeH containing amino acid, peptide, or peptidomimetic. In certain embodiments, the —SH or —SeH containing amino acid, peptide, or peptidomimetic is selected from the group consisting of Captopril, Zofenopril, Tiopronin, Penicillamine, L-Cysteine, Selenocysteine, Gluthatione, Thiorphan, Bucillamine, Omapatrilat, Pantetheine, or Mycothiol.

In certain embodiments, the agent is a —SH or —SeH containing aryl or heteroaryl compound. In certain embodiments, the —SH or —SeH containing aryl or heteroaryl compound is selected from the group consisting of Furan-2-ylmethanethiol, Ovothiol A, Rentiapril, or Thiosalicylic acid.

In certain embodiments, the agent comprises a disulfide bond. In certain embodiments, the agent is selected from the group consisting of disulfiram, Psammaplin A, Dixanthogen, Pantethine, Fursultiamine, Octotiamine, Sulbutiamine, Prosultiamine, Thiram, Lipoic acid, Lenthionine, Ajoene, Allicin, Gemopatrilat, and Sulfanegen. Each possibility represents a separate embodiment of the invention.

In certain embodiments, the ophthalmically-acceptable carrier comprises at least one ophthalmically-acceptable excipient.

In certain embodiments, the methods described above further comprise the step of administering to the patient a keratolytic agent. In certain embodiments, the keratolytic agent is selected from the group consisting of benzoyl peroxide, coal tar, dithranol, salicylic acid, selenium disulfide, alpha-hydroxy acid, urea, boric acid, retinoic acid, lactic acid, sodium thioglycolate or allantoin.

In certain embodiments, the meibomian gland dysfunction is characterized by obstruction of a meibomian gland. In certain embodiments, the topical administration of the agent to the eyelid margin of the patient is repeated until the meibomian gland obstruction is substantially removed. In certain embodiments, the topical administration of the agent to the eyelid margin of the patient is periodically repeated to prevent formation of a meibomian gland obstruction.

In certain embodiments, the methods described above result in a therapeutically effective increase in the quantity of lipids produced by the meibomian gland. In certain embodiments, the methods described above result in a therapeutically effective increase in the quantity of lipids secreted from the meibomian gland. In certain embodiments, the methods described above result in an alternation of the composition of lipids secreted by meibomian gland. In certain embodiments, the methods described above result in an alternation, preferably reduction, of the viscosity of lipids secreted by meibomian gland.

In some embodiments, the active agents are formulated and applied such that they are acceptable to the surface of the eye (i.e. not causing undue irritation or disruption to the epithelial surface of the eye), and do not compromise lipid producing cells in contact with the composition.

In some embodiments, the composition is applied for a duration and frequency that is acceptable and practical to the physician or patient administering the agent. For example, a physician applies a composition described herein weekly or twice a week for several weeks to induce increase in the quantity of lipids secreted from the meibomian gland and the patient applies a different composition on a daily basis, or the patient uses a more potent composition on a daily basis for several weeks and then, subsequently uses a less potent composition of a daily basis thereafter. In some embodiments, the composition is applied by the patient on a daily basis once or several times a day.

In some embodiments, the method of application varies, depending on the concentration of the agent and/or the extent of lipid deficiency. In other embodiments, the method of application of the composition is tailored to enhance the penetration or residency time on the target tissue in order to enhance the effect of the treatment. In other embodiments, the method of application of the composition is varied to enhance the penetration or residency time on the target tissue to minimize the amount of application time necessary. In other embodiments, the composition is formulated (e.g., by adjusting viscosity and/or skin-adhesiveness) to increase contact with the target tissue while minimizing contact with non-target tissues, including the eye, and thus limit or reduce any undesired collateral activity.

In certain embodiments, the concentration of the agent and of the excipients is optimized to deliver the minimum effective concentration of the agent to achieve the therapeutic benefit while minimizing any ocular irritation or disruption, or irritation or disruption to surrounding ocular tissues.

The methods and compositions described herein are means for increasing the quantity of lipids secreted from meibomian glands, altering the composition of the lipids secreted by the meibomian glands, and/or reducing the viscosity of lipids secreted from meibomian glands, thereby enhancing the dissolution of any meibomian gland obstruction and improving tear breakup time (TBUT).

The compositions used in the methods of the present invention include at least one lipogenesis and lipid secretion enhancing thiol-containing, —SeH containing, or disulfide-containing agent. In some embodiments, the agent is a thiol-containing, —SeH containing, drug that causes increased meibum production. In some embodiments, the agent is a thiol-containing, —SeH containing, drug such as Captopril, Zofenopril, Tiopronin, Penicillamine, L-Cysteine, Selenocysteine, Gluthatione, Dithiothreitol, Thiorphan, Cysteamine, Bucillamine, Dimercaprol, 1,1-Ethanedithiol, Dimercaptosuccinic acid, Furan-2-ylmethanethiol, Omapatrilat, Ovothiol A, Pantetheine, Rentiapril, Thiosalicylic acid, Tixocortol, Mycothiol, Coenzyme A, Coenzyme B. Their chemical structures are presented in Table 2.

TABLE 2

Chemical structures of certain thiol-containing, or —SeH containing drugs.

Captopril

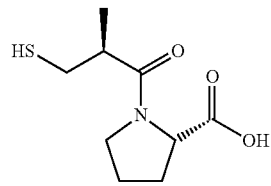

TABLE 2-continued
Chemical structures of certain thiol-containing, or —SeH containing drugs.
Zofenopril
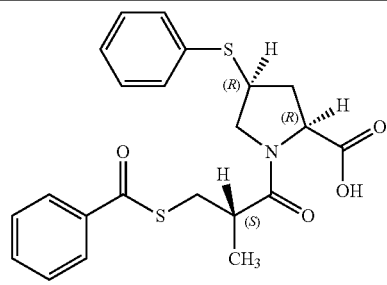
Tiopronin
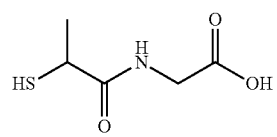
Penicillamine
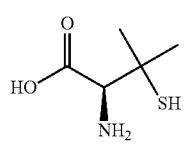
Selenocysteine
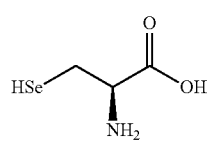
L-cysteine
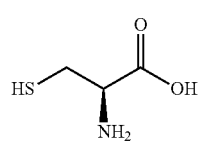
Gluthatione
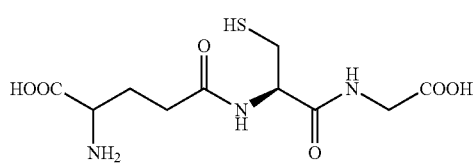 [SMILES: NC(CCC(=O)N[C@@H](CS)C(=O)NCC(=O)O)C(=O)O]
Dithiothreitol
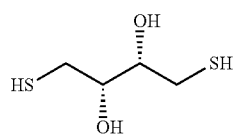
Thiorphan
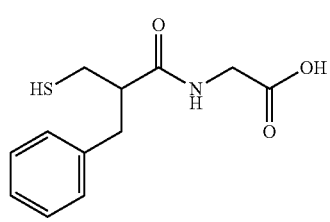 [SMILES: O=C(O)CNC(=O)C(CS)Cc1ccccc1]
Cysteamine
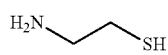
Bucillamine
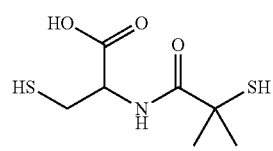

TABLE 2-continued
Chemical structures of certain thiol-containing, or —SeH containing drugs.
| | |
|---|---|
| Dimercaprol | 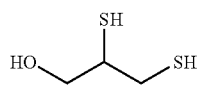 |
| 1,1-Ethanedithiol | 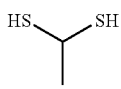 |
| Dimercaptosuccinic acid | 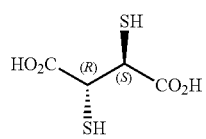 |
| Furan-2-ylmethanethiol | 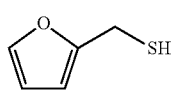 |
| Omapatrilat | 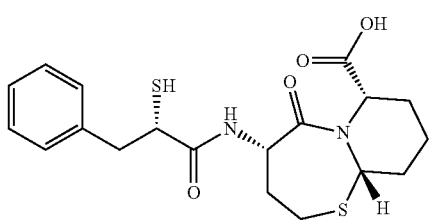 [SMILES: O=C(N[C@H]1CCS[C@H]2CCC[C@@H](C(=O)O)N2C1=O)[C@@H](S)Cc1ccccc1] |
| Ovothiol A | 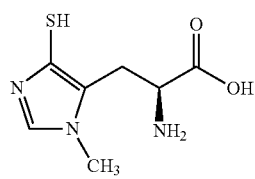 |
| Pantetheine | 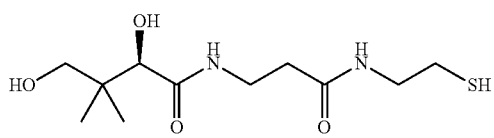 [SMILES: CC(C)(CO)[C@@H](O)C(=O)NCCC(=O)NCCS] |
| Rentiapril | 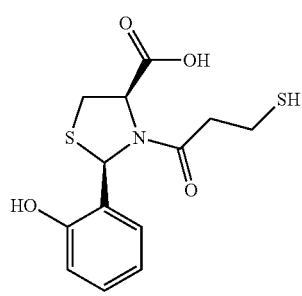 [SMILES: O=C(O)[C@@H]1CS[C@H](c2ccccc2O)N1C(=O)CCS] |
| Thiosalicyclic acid | 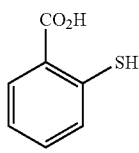 |

TABLE 2-continued
Chemical structures of certain thiol-containing, or —SeH containing drugs.
Tixocortol
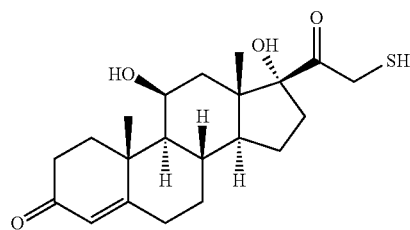
Mycothiol
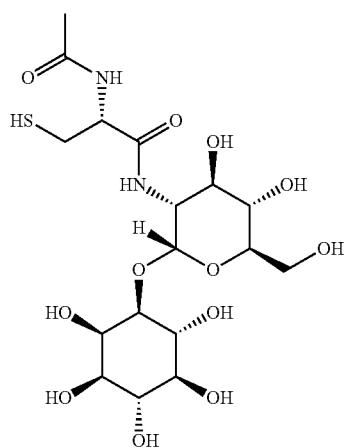 [SMILES: CC(=O)N[C@@H](CS)C(=O)N[C@H]1[C@@H](O[C@@H]2[C@H](O)[C@H](O)[C@@H](O)[C@H](O)[C@H]2O)O[C@H](CO)[C@@H](O)[C@@H]1O]
Coenzyme A
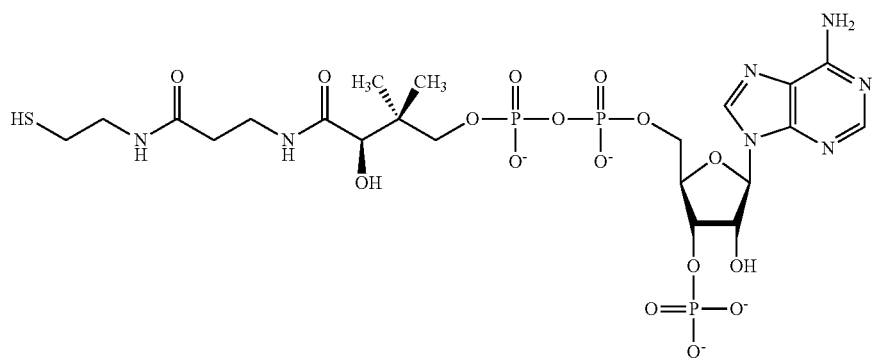
Coenzyme B
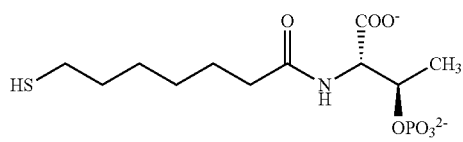
Gemopatrilat
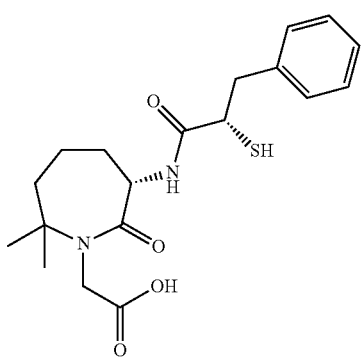 [SMILES: CC1(C)CCC[C@H](NC(=O)[C@@H](S)Cc2ccccc2)C(=O)N1CC(=O)O]

TABLE 2-continued

Chemical structures of certain thiol-containing, or —SeH containing drugs.

Sulfanegen

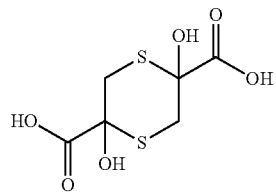 [SMILES: O=C(O)C1(O)CSC(O)(C(=O)O)CS1]

Selenium D-methionine

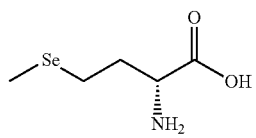

In some embodiments, the agent is a disulfide containing drug such as disulfiram, Psammaplin A, Dixanthogen, Pantethine, Fursultiamine, Octotiamine, Sulbutiamine, Prosultiamine, Thiram, Lipoic acid, Lenthionine, Ajoene, Allicin, Gemopatrilat, and Sulfanegen. Their chemical structures are presented in Table 3.

TABLE 3

Chemical structures of disulfide containing drugs.

Disulfiram

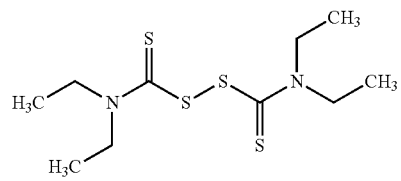 [SMILES: CCN(CC)C(=S)SSC(=S)N(CC)CC]

Psammaplin A

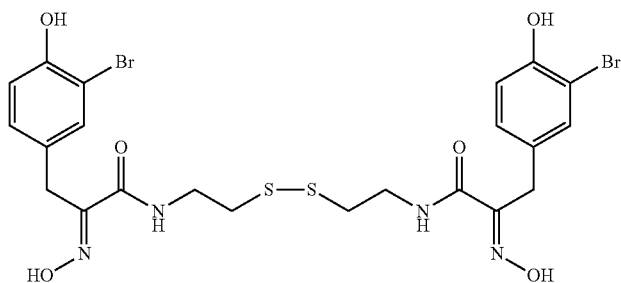 [SMILES: O=C(NCCSSCCNC(=O)/C(Cc1ccc(O)c(Br)c1)=N/O)/C(Cc1ccc(O)c(Br)c1)=N/O]

Dixanthogen

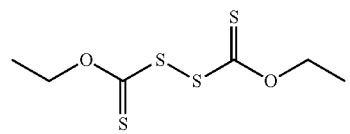

Pantethine

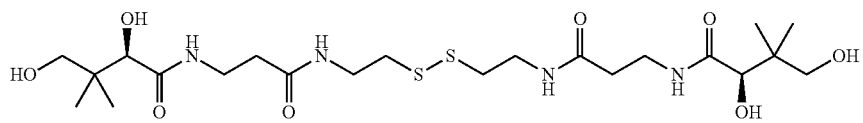 [SMILES: CC(C)(CO)[C@@H](O)C(=O)NCCC(=O)NCCSSCCNC(=O)CCNC(=O)[C@H](O)C(C)(C)CO]

Fursultiamine

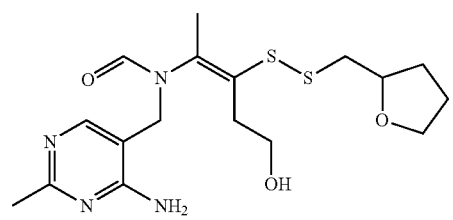 [SMILES: C/C(=C(/CCO)SSCC1CCCO1)N(C=O)Cc1cnc(C)nc1N]

TABLE 3-continued
Chemical structures of disulfide containing drugs.
Octotiamine
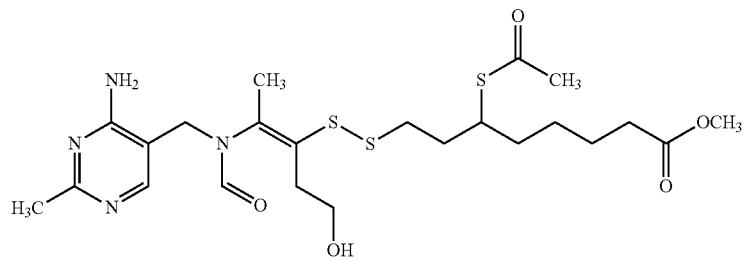 [SMILES: COC(=O)CCCCC(CCSS/C(CCO)=C(\C)N(C=O)Cc1cnc(C)nc1N)SC(C)=O]
Sulbutiamine
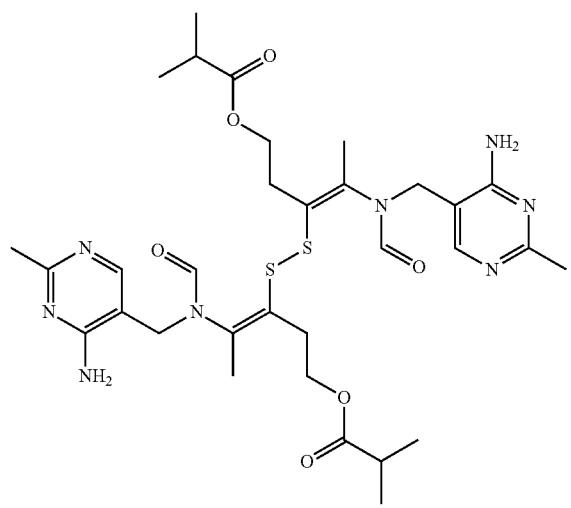
Prosultiamine
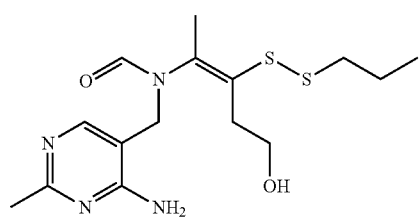 [SMILES: CCCSS/C(CCO)=C(\C)N(C=O)Cc1cnc(C)nc1N]
Thiram
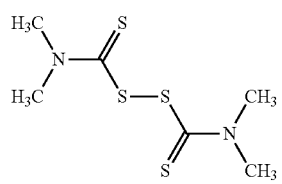
Lipoic acid
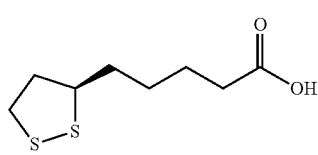 [SMILES: O=C(O)CCCC[C@@H]1CCSS1]
Lenthionine
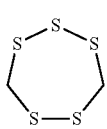
Ajoene
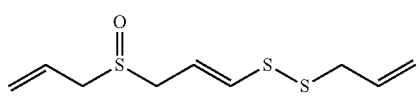

TABLE 3-continued

Chemical structures of disulfide containing drugs.

Allicin

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is Captopril.

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is Zofenopril.

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is Tiopronin.

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is Penicillamine.

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is L-Cysteine.

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is Selenocysteine.

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is Gluthatione.

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is Dithiothreitol.

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is Thiorphan.

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is Cysteamine.

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is Bucillamine.

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is Dimercaprol.

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is 1,1-Ethanedithiol.

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is Dimercaptosuccinic acid.

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is Furan-2-ylmethanethiol.

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is Omapatrilat.

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is Ovothiol A.

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is Pantetheine.

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is Rentiapril.

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is Thiosalicylic acid.

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is Tixocortol.

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is Mycothiol.

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is Coenzyme A.

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is Coenzyme B.

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is Gemopatrilat.

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is Sulfanegen.

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is Selenium D-methionine.

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is disulfiram.

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is Psammaplin A.

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is Dixanthogen.

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is Pantethine.

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is Fursultiamine.

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is Octotiamine.

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is Sulbutiamine.

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is Prosultiamine.

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is Thiram.

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is Lipoic acid.

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is Lenthionine.

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is Ajoene.

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is Allicin.

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is Gemopatrilat.

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is Sulfanegen.

The present invention provides, for the first time, derivatives of lipids containing sulfhydryl groups and/or disulfides, useful for enhancing the secretion of the meibum lipids in-vivo, and in treating meibomian gland dysfunction (MGD).

More specifically, also described herein are methods for enhancing lipogenesis in meibomian glands, for lowering the melting point of lipids secreted from meibomian glands, for reducing the viscosity of lipids secreted from meibomian glands, and for reducing the viscosity of lipids in the eyelid margins, by administering thiol-containing or disulfide-containing lipid derivatives. The lipid derivatives described herein include lipid derivatives for acute therapies, for use, e.g., by a physician or other trained specialist, and lipid derivatives for chronic therapies, e.g., either by a physician or other trained specialist, or by the patient. Certain lipid derivatives are described herein; further provided herein are methods for preparing lipid derivatives as well as their use in methods of treatment of patients.

According to the principles of the present invention, thiol-containing or disulfide-containing lipid derivatives which induce lipogenesis and meibum lipid secretion, can be used, e.g., as treatment for MGD through thiol-mediated lipid over-secretion mechanisms. More according to the principles of the present invention, disulfide containing lipid derivatives, present thiol or sulfhydryl radicals once the disulfide bond is cleaved within the body by enzymes or chemical reactions.

Lipid derivatives-induced activation of cellular lipogenesis thus represents a new approach for therapeutic treatment of MGD through enhanced synthesis of cholesterol and increased production of fatty acids and triglycerides that lead to alterations in composition of the meibum lipids, by decreasing the melting point and viscosity of the meibum lipids, which results in a more fluid appearance of meibum lipids.

The lipogenesis and lipid secretion enhancing lipid derivatives described herein are useful either as an acute therapy (e.g., by a trained specialist or physician) or as a chronic therapy (e.g., in the hands of a patient, or alternatively, by a trained specialist or physician). The agents are tested, in certain embodiments, using the assays and methods described herein (e.g., as described in the examples).

The present invention provides, in one aspect, a method for increasing lipid secretion from a meibomian gland, comprising topically administering to the eyelid margin of the patient in need thereof an ophthalmic composition comprising an ophthalmically-acceptable carrier and an effective amount of at least one lipid-derivative comprising a sulfhydryl group or a disulfide.

The present invention further provides, in another aspect, a method for treating MGD, comprising topically administering to the eyelid margin of the patient in need thereof an ophthalmic composition comprising an ophthalmically-acceptable carrier and a therapeutically-effective amount of at least one lipid-derivative comprising a sulfhydryl group or a disulfide.

The present invention further provides, in another aspect, a method for increasing lipid production in a meibomian gland, comprising topically administering to the eyelid margin of the patient in need thereof an ophthalmic composition comprising an ophthalmically-acceptable carrier and an effective amount of at least one lipid-derivative comprising a sulfhydryl group or a disulfide.

The present invention further provides, in another aspect, a method for lowering the melting point of lipids secreted from a meibomian gland, comprising topically administering to the eyelid margin of the patient in need thereof an ophthalmic composition comprising an ophthalmically-acceptable carrier and an effective amount of at least one lipid-derivative comprising a sulfhydryl group or a disulfide.

The present invention further provides, in another aspect, a method for reducing the viscosity of lipids secreted from a meibomian gland, comprising topically administering to the eyelid margin of the patient in need thereof an ophthalmic composition comprising an ophthalmically-acceptable carrier and an effective amount of at least one lipid-derivative comprising a sulfhydryl group or a disulfide.

The present invention further provides, in another aspect, a method for reducing the viscosity of lipids in an eyelid margin, comprising topically administering to the eyelid margin of the patient in need thereof an ophthalmic composition comprising an ophthalmically-acceptable carrier and an effective amount of at least one lipid-derivative comprising a sulfhydryl group or a disulfide.

In certain embodiments, the lipid-derivative is a derivative of a lipid selected from the group consisting of a fatty acid, a glycerolipid, a glycerophospholipid, a sphingolipid, a sterol lipid, a prenol lipid, a saccharolipid, a polyketide, and any combination thereof. Each possibility represents a separate embodiment of the invention. In certain embodiments, the lipid-derivative is a derivative of a lipid found naturally in the meibum.

In some embodiments, the lipid derivative is a lipid containing a —S—H or disulfide such as Thiophospholipid, Thiocholesterol, 12-Mercaptododecanoic acid or 23-(9-Mercaptononyl)-3,6,9,12,15,18,21-Heptaoxatricosanoic Acid.

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is Thiophospholipid.

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is Thiocholesterol.

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is 12-Mercaptododecanoic acid.

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is 23-(9-Mercaptononyl)-3,6,9,12,15,18,21-Heptaoxatricosanoic Acid.

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is Thioethanol.

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is selenium disulfide.

In certain embodiments, the lipid is selected from the group consisting of a fatty acid, a wax ester, a cholesterol ester, a tri-glyceride, a di-glyceride, a mono-glyceride, a phospholipid, a diester, a fatty acid amide, squalene, a ceramide, a sphingolipid, a w-hydroxy fatty acid, cholesterol, and epoxides thereof. Each possibility represents a separate embodiment of the invention.

In certain embodiments, the fatty acid has a molecular formula selected from the group consisting of: (i) $C_nH_{2n}O_2$, wherein n is any integer selected from 12, 14-18 and 20-29; (ii) $C_nH_{2n-2}O_2$, wherein n is any integer selected from 16-18, 20, 22, 24, 26, 28, 30 and 32; and (iii) $C_nH_{2n-4}O_2$, wherein n is 18. In certain embodiments, the fatty acid is selected from the group consisting of myristic acid, palmitic acid, stearic acid, and oleic acid. Each possibility represents a separate embodiment of the invention.

In certain embodiments, the wax ester is an oleic acid ester of a saturated $C_{18-30}$ fatty acid. In certain embodiments, the cholesterol ester is a cholesterol ester of a $C_{16-34}$ fatty acid. Each possibility represents a separate embodiment of the invention.

In certain embodiments, the triglyceride has a molecular formula selected from the group consisting of: (i) $C_nH_{2n-8}O_6$, wherein n is any integer selected from 55 and 57; (ii) $C_nH_{2n-10}O_6$, wherein n is any integer selected from 55 and 57; and (iii) fatty acids chains associated with the triglycerides: C14:0, C15:0, C16:0, C16:1, C17:0, C18:0, C18:1, C18:2.9. Each possibility represents a separate embodiment of the invention.

In certain embodiments, the phospholipid is selected from the group consisting of phosphatidylcholine (PC), phosphatidylethanolamine (PE), alkylacylphosphatidylcholine, sphingomyelin, dihydrosphingomyelin, dimethylphosphatidylethanolamine, diphosphatidylglycerol (cardiolipin), ethanolamine plasmalogen, lysoethanolamine plasmalogen, lysophosphatidylcholine, lysophosphatidylethanolamine, lysophosphatidylserine, phosphatidic acid, phosphatidylglycerol, phosphatidylinositol, and phosphatidylserine. Each possibility represents a separate embodiment of the invention.

In certain embodiments, the fatty acid amide is selected from the group consisting of oleamide, myristamide, palmitamide, stearamide, and erucamide. Each possibility represents a separate embodiment of the invention.

In certain embodiments, the w-hydroxy fatty acid has a molecular formula selected from the group consisting of: (i) $C_nH_{2n-7}O_4$, wherein n is any integer selected from 46-52; (ii) $C_nH_{2n-4}O_4$, wherein n is any integer selected from 42-50; (iii) $C_nH_{2n-6}O_4$, wherein n is any integer selected from 42, 44, 46, and 48-52; (iv) $C_nH_{2n-8}O_4$, wherein n is any integer selected from 48, 50, and 52; and (v) $C_nH_{2n-10}O_4$, wherein n is any integer selected from 50 and 52. Each possibility represents a separate embodiment of the invention.

In certain embodiments, the lipid-derivative is polar. In certain embodiments, the lipid-derivative is non-polar. In certain embodiments, the lipid-derivative comprises sulfhydryl group. In certain embodiments, the lipid-derivative comprises a disulfide.

In certain embodiments, the methods described above further comprise the step of administering to the patient a keratolytic agent. In certain embodiments, the keratolytic agent is selected from the group consisting benzoyl peroxide, coal tar, dithranol, salicylic acid, selenium disulfide, alpha-hydroxy acid, urea, boric acid, retinoic acid, lactic acid, sodium thioglycolate or allantoin. Each possibility represents a separate embodiment of the invention.

In certain embodiments, the meibomian gland dysfunction is characterized by obstruction of a meibomian gland. In certain embodiments, the topical administration of the lipid-derivative to the eyelid margin of the patient is repeated until the meibomian gland obstruction is substantially removed. In certain embodiments, the topical administration of the lipid-derivative to the eyelid margin of the patient is periodically repeated to prevent formation of a meibomian gland obstruction.

One embodiment provides a method for increasing lipid secretion from a meibomian gland, comprising topically administering to the eyelid margin of the patient in need thereof an ophthalmic composition comprising an ophthalmically-acceptable carrier and an effective amount of at least one lipid-derivative comprising a sulfhydryl group or a disulfide.

Another embodiment provides the method for increasing lipid secretion from a meibomian gland, wherein the lipid-derivative is a derivative of a lipid selected from the group consisting of a fatty acid, a glycerolipid, a glycerophospholipid, a sphingolipid, a sterol lipid, a prenol lipid, a saccharolipid, a polyketide, and any combination thereof.

Another embodiment provides the method for increasing lipid secretion from a meibomian gland, wherein the lipid-derivative is a derivative of a lipid found naturally in the meibum.

Another embodiment provides the method for increasing lipid secretion from a meibomian gland, wherein the lipid is selected from the group consisting of a fatty acid, a wax ester, a cholesterol ester, a tri-glyceride, a di-glyceride, a mono-glyceride, a phospholipid, a diester, a fatty acid amide, squalene, a ceramide, a sphingolipid, a w-hydroxy fatty acid, cholesterol, and epoxides thereof.

Another embodiment provides the method for increasing lipid secretion from a meibomian gland wherein the lipid is a fatty acid and the fatty acid has a molecular formula selected from the group consisting of: (i) $C_nH_{2n}O_2$, wherein n is any integer selected from 12, 14-18 and 20-29; (ii) $C_nH_{2n-2}O_2$, wherein n is any integer selected from 16-18, 20, 22, 24, 26, 28, 30 and 32; and (iii) $C_nH_{2n-4}O_2$, wherein n is 18.

Another embodiment provides the method for increasing lipid secretion from a meibomian gland wherein the lipid is a fatty acid and the fatty acid is selected from the group consisting of myristic acid, palmitic acid, stearic acid, and oleic acid.

Another embodiment provides the method for increasing lipid secretion from a meibomian gland wherein the lipid is a wax ester and the wax ester is an oleic acid ester of a saturated $C_{18-30}$ fatty acid.

Another embodiment provides the method for increasing lipid secretion from a meibomian gland wherein the lipid is a cholesterol ester and the cholesterol ester is a cholesterol ester of a $C_{16-34}$ fatty acid.

Another embodiment provides the method for increasing lipid secretion from a meibomian gland wherein the lipid is a triglyceride and the triglyceride has a molecular formula selected from the group consisting of: (i) $C_nH_{2n-8}O_6$, wherein n is any integer selected from 55 and 57; (ii) $C_nH_{2n-10}O_6$, wherein n is any integer selected from 55 and 57; and (iii) fatty acids chains associated with the triglycerides: C14:0, C15:0, C16:0, C16:1, C17:0, C18:0, C18:1, C18:2.9.

Another embodiment provides the method for increasing lipid secretion from a meibomian gland wherein the lipid is a phospholipid and the phospholipid is selected from the group consisting of phosphatidylcholine (PC), phosphatidylethanolamine (PE), alkylacylphosphatidylcholine, sphingomyelin, dihydrosphingomyelin, dimethylphosphatidylethanolamine, diphosphatidylglycerol (cardiolipin), ethanolamine plasmalogen, lysoethanolamine plasmalogen, lysophosphatidylcholine, lysophosphatidylethanolamine, lysophosphatidylserine, phosphatidic acid, phosphatidylglycerol, phosphatidylinositol, and phosphatidylserine.

Another embodiment provides the method for increasing lipid secretion from a meibomian gland wherein the lipid is a fatty acid amide and the fatty acid amide is selected from the group consisting of oleamide, myristamide, palmitamide, stearamide, erucamide and ceramide.

Another embodiment provides the method for increasing lipid secretion from a meibomian gland wherein the lipid is a w-hydroxy fatty acid and the w-hydroxy fatty acid has a molecular formula selected from the group consisting of: (i) $C_nH_{2n-7}O_4$, wherein n is any integer selected from 46-52; (ii) $C_nH_{2n-4}O_4$, wherein n is any integer selected from 42-50; (iii) $C_nH_{2n-6}O_4$, wherein n is any integer selected from 42, 44, 46, and 48-52; (iv) $C_nH_{2n-8}O_4$, wherein n is any integer selected from 48, 50, and 52; and (v) $C_nH_{2n-10}O_4$, wherein n is any integer selected from 50 and 52.

Another embodiment provides the method for increasing lipid secretion from a meibomian gland wherein the lipid-derivative is polar. Another embodiment provides the method wherein the lipid-derivative is non-polar. Another embodiment provides the method wherein the lipid-derivative comprises sulfhydryl group. Another embodiment provides the method wherein the lipid-derivative comprises a disulfide.

Another embodiment provides the method for increasing lipid secretion from a meibomian gland wherein the ophthalmically-acceptable carrier comprises at least one ophthalmically-acceptable excipient.

One embodiment provides a method for increasing lipid secretion from a meibomian gland, comprising topically administering to the eyelid margin of the patient in need thereof an ophthalmic composition comprising an ophthalmically-acceptable carrier and an effective amount of at least one lipid-derivative comprising a sulfhydryl group or a disulfide, wherein the method further comprises the step of administering to the patient a keratolytic agent. Another embodiment provides the method wherein the keratolytic agent is selected from the group consisting of selenium sulfide, dithranol, benzoyl peroxide, urea, salicilyc acid, boric acid, lactic acid, retinoic acid, and an alpha-hydroxy acid.

One embodiment provides a method for treating meibomian gland dysfunction (MGD), comprising topically administering to the eyelid margin of the patient in need thereof an ophthalmic composition comprising an ophthalmically-acceptable carrier and a therapeutically-effective amount of at least one lipid-derivative comprising a sulfhydryl group or a disulfide.

Another embodiment provides the method for treating meibomian gland dysfunction (MGD), wherein the lipid-derivative is a derivative of a lipid selected from the group consisting of a fatty acid, a glycerolipid, a glycerophospholipid, a sphingolipid, a sterol lipid, a prenol lipid, a saccharolipid, a polyketide, and any combination thereof.

Another embodiment provides the method for treating meibomian gland dysfunction (MGD), wherein the lipid-derivative is a derivative of a lipid found naturally in the meibum.

One embodiment provides a method for treating meibomian gland dysfunction (MGD), comprising topically administering to the eyelid margin of the patient in need thereof an ophthalmic composition comprising an ophthalmically-acceptable carrier and a therapeutically-effective amount of at least one lipid-derivative comprising a sulfhydryl group or a disulfide, wherein the method further comprises the step of administering to the patient a keratolytic agent. One embodiment provides a method for treating meibomian gland dysfunction (MGD) wherein the keratolytic agent is selected from the group consisting of selenium sulfide, dithranol, benzoyl peroxide, urea, salicylic acid, boric acid, lactic acid, retinoic acid, and an alpha-hydroxy acid. Another embodiment provides the method for treating meibomian gland dysfunction (MGD) wherein the meibomian gland dysfunction is characterized by obstruction of a meibomian gland. Another embodiment provides the method for treating meibomian gland dysfunction (MGD) wherein the topical administration of the lipid-derivative to the eyelid margin of the patient is repeated until the meibomian gland obstruction is substantially removed. Another embodiment provides the method for treating meibomian gland dysfunction (MGD) wherein the topical administration of the lipid-derivative to the eyelid margin of the patient is periodically repeated to prevent formation of a meibomian gland obstruction. Another embodiment provides the method for treating meibomian gland dysfunction (MGD) wherein the ophthalmically-acceptable carrier comprises at least one ophthalmically-acceptable excipient.

In certain embodiments, the methods described above result in a significant, preferably statistically significant increase in the quantity of lipids produced by the meibomian gland. In certain embodiments, the methods described above result in a significant, preferably statistically significant increase in the quantity of lipids secreted from the meibomian gland. In certain embodiments, the methods described above result in a significant, preferably statistically significant alternation of the composition of lipids secreted by the meibomian gland. In certain embodiments, the methods described above result in a significant, preferably statistically significant alternation, preferably reduction, of the melting point of lipids secreted from the meibomian gland. In certain embodiments, the methods described above result in a significant, preferably statistically significant alternation, preferably reduction, of the viscosity of lipids secreted by the meibomian gland. In certain embodiments, the methods described above result in a significant, preferably statistically significant alternation, preferably reduction, of the viscosity of lipids in the eyelid margin.

In certain embodiments, the methods described above result in a therapeutically effective increase in the quantity of lipids produced by the meibomian gland. In certain embodiments, the methods described above result in a therapeutically effective increase in the quantity of lipids secreted from the meibomian gland. In certain embodiments, the methods described above result in a therapeutically effective alternation of the composition of lipids secreted by the meibomian gland. In certain embodiments, the methods described above result in a therapeutically effective alternation, preferably reduction, of the melting point of lipids secreted from the meibomian gland. In certain embodiments, the methods described above result in a therapeutically effective alternation, preferably reduction, of the viscosity of lipids secreted by the meibomian gland. In certain embodiments, the methods described above result in a therapeutically effective alternation, preferably reduction, of the viscosity of lipids in the eyelid margin.

In some embodiments, the active agents are formulated and applied such that they are acceptable to the surface of the eye (i.e. not causing undue irritation or disruption to the epithelial surface of the eye), and do not compromise lipid producing cells in contact with the composition.

In some embodiments, the composition is applied for a duration and frequency that is acceptable and practical to the physician or patient administering the agent. For example, a physician applies a composition described herein weekly or twice a week for several weeks to induce increase in the quantity of lipids secreted from the meibomian gland and the patient applies a different composition on a daily basis, or the patient uses a more potent composition on a daily basis for several weeks and then, subsequently uses a less potent composition of a daily basis thereafter. In some embodiments, the composition is applied by the patient on a daily basis once or several times a day.

In some embodiments, the method of application varies, depending on the concentration of the lipid-derivative and/or the extent of lipid deficiency. In other embodiments, the method of application of the composition is tailored to enhance the penetration or residency time on the target tissue in order to enhance the effect of the treatment. In other embodiments, the method of application of the composition is varied to enhance the penetration or residency time on the target tissue to minimize the amount of application time necessary. In other embodiments, the composition is formulated (e.g., by adjusting viscosity and/or skin-adhesiveness) to increase contact with the target tissue while minimizing contact with non-target tissues, including the eye, and thus limit or reduce any undesired collateral activity.

In certain embodiments, the concentration of the lipid-derivative and of the excipients is optimized to deliver the minimum effective concentration of the lipid-derivative to achieve the therapeutic benefit while minimizing any ocular irritation or disruption, or irritation or disruption to surrounding ocular tissues.

The methods and compositions described herein are means for increasing the quantity of lipids secreted from meibomian glands, altering the composition of the lipids secreted by the meibomian glands, and/or reducing the viscosity of lipids secreted from meibomian glands, thereby enhancing the dissolution of any meibomian gland obstruction and improving tear breakup time (TBUT).

In some embodiments, topical administration of at least one lipid-derivative twice a week. In some embodiments, topical administration of at least one lipid-derivative occurs every other day. In some embodiments, topical administration of at least one lipid-derivative occurs every day. In some embodiments, topical administration of at least one lipid-derivative occurs several times a day.

In some embodiments, the composition for topical administration is a liquid or a semi-solid. In some embodiments, the composition for topical administration is a semi-solid emulsion. In some embodiments, the composition for topical administration is a cream. In some embodiments, the composition for topical administration is an ointment. In some embodiments, the lipid-derivative is suspended or dispersed within the composition. In some embodiments, the composition for topical administration is a lotion. In some embodiments, the composition for topical administration is a gel.

One embodiment provides a method for treating MGD in a patient in need thereof by topical administration of a composition comprising at least one lipid-derivative, wherein the treatment results in a therapeutically-relevant increase in the quantity of lipids produced by the meibomian gland. One embodiment provides a method for treating MGD in a patient in need thereof by topical administration of a composition comprising at least one lipid-derivative, wherein the treatment results in a therapeutically-relevant increase in the quantity of lipids secreted from the meibomian gland. Another embodiment provides a method for treating MGD in a patient in need thereof by topical administration of a composition comprising a lipid-derivative, wherein the treatment results in a therapeutically-relevant increase of meibum production. Another embodiment provides a method for treating MGD in a patient in need thereof by topical administration of a composition comprising lipid-derivative, wherein the treatment results in a therapeutically-relevant change in the meibum lipids' composition. Another embodiment provides a method for treating MGD in a patient in need thereof by topical administration of a composition comprising lipid-derivative, wherein the treatment results in a therapeutically-relevant decrease in the melting point of lipids secreted from the meibomian gland. Another embodiment provides a method for treating MGD in a patient in need thereof by topical administration of a composition comprising lipid-derivative, wherein the treatment results in a therapeutically-relevant decrease in the viscosity of lipids secreted from the meibomian gland. Another embodiment provides a method for treating MGD in a patient in need thereof by topical administration of a composition comprising lipid-derivative, wherein the treatment results in a therapeutically-relevant decrease in the viscosity of lipids in the eyelid margin.

In any of the aforementioned embodiments, the composition further comprises an ophthalmically-acceptable carrier. In one further embodiment, the ophthalmically-acceptable carrier comprises an ophthalmically-acceptable excipient. In certain embodiments, the ophthalmically-acceptable carrier comprises a plurality of ophthalmically-acceptable excipients. Such excipients are described, for example, in Remington: The Science and Practice of Pharmacy (Gennaro, 21$^{st}$ Ed. Mack Pub. Co., Easton, Pa. (2005)).

One embodiment provides a method for enhancing lipogenesis and lipid secretion from a meibomian gland in a patient in need thereof by administering a topical composition comprising a lipid-derivative, wherein the composition comprises 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.5%, 5%, or 10% of the lipid-derivative. In some embodiments, the composition is formulated as a suspension, emulsion, cream, lotion, gel, or ointment. In some embodiments, the composition is applied as a thin layer to clean skin initially once daily on alternate days, and is then gradually increased up to twice daily as tolerance develops. In some embodiments, the composition is an ointment or paste. In some embodiments, the composition is started as a 0.1% ointment. After 7 days, the concentration may be increased to 0.25% and subsequently doubled, if necessary, at weekly intervals to a maximum strength of 2%. In some embodiments, a thin layer of ointment is applied once daily to the affected areas for 2-4 weeks. In some embodiments, the ointment is left in place for 10 to 20 minutes before the area is rinsed thoroughly. In some embodiments, the concentration of lipogenesis and lipid secretion enhancing thiol-containing or disulfide-containing drug or pharmaceutical agent is gradually increased to a maximum of 5%, and treatment is continued for as long as necessary.

In some embodiments, the topical administration of the composition comprising a lipid-derivative occurs once a week. In some embodiments, the topical administration of the composition comprising a lipid-derivative occurs twice a week. In some embodiments, the topical administration of the composition comprising a lipid-derivative occurs every other day. In some embodiments, the topical administration of the composition comprising a lipid-derivative occurs every day. In some embodiments, the topical administration of the composition comprising a lipid-derivative occurs several times a day.

In some embodiment, the method comprises treatment in an acute treatment scenario. In another embodiment, the method comprises treatment of a patient naïve to similar or identical treatment. In another embodiment, the method comprises treatment in a chronic treatment scenario. In another embodiment, the method comprises treatment in a maintenance therapy scenario. In an acute treatment scenario, the administered dosage of lipid-derivatives may be higher than the administered dosage of lipid-derivatives employed in a chronic treatment scenario or a maintenance therapy scenario. In an acute treatment scenario, the lipid-derivatives may be different from the lipid-derivatives employed in a chronic treatment scenario. In some embodiments, the course of therapy begins in the initial phase of therapy as an acute treatment scenario and later transitions into a chronic treatment scenario or a maintenance therapy scenario.

In some embodiments, the agent is the active agent responsible for increasing the quantity of lipids secreted from meibomian gland, altering the composition of the lipids secreted by the meibomian gland, and/or reducing the viscosity of the lipids secreted by the meibomian gland, thereby enhancing the dissolution of any meibomian gland obstruction.

In some embodiments, topical administration of at least one agent occurs twice a week. In some embodiments, topical administration of at least one agent occurs every other day. In some embodiments, topical administration of at least one agent occurs every day. In some embodiments, topical administration of at least one agent occurs several times a day.

In some embodiments, the composition for topical administration is a liquid or a semi-solid. In some embodiments, the composition for topical administration is a semi-solid emulsion. In some embodiments, the composition for topical administration is a cream. In some embodiments, the composition for topical administration is an ointment. In some embodiments, the agent is suspended or dispersed within the composition. In some embodiments, the composition for topical administration is a lotion. In some embodiments, the composition for topical administration is a gel.

Pharmaceutical acceptable topical compositions are prepared containing the lipogenesis and lipid secretion enhancing thiol-containing, —SeH containing, or disulfide-containing drug or pharmaceutical agent. The gels are mainly hydrophilic and optionally contain suspending agent, dispersing agent, solubilizing agent, emulsifying agent, thickening agent, preservative, antioxidant at the desired acceptable concentrations for ophthalmic preparations. The ophthalmic ointments are primarily anhydrous and contain mineral oil and white petrolatum as the base ingredients. The petrolatum base can be made more miscible with aqueous components by addition of lanolin. Exemplary lipogenesis and lipid secretion enhancing formulations described herein further contain suspending agents, emulsifying agents, solubilizing agents or thickening agents.

Suspending agents: A suspending agent helps to reduce the sedimentation rate of particles in suspension. These are insoluble particles that are dispersed in a liquid vehicle. The suspending agent works by increasing the viscosity of the liquid vehicle, and thereby slowing down settling in accordance with Stokes Law. Most suspending agents perform two functions. Besides acting as a suspending agent they also imparts viscosity to the solution. Suspending agents form film around particle and decrease inter-particle attraction. Suspending agents also act as thickening agents. They increase in viscosity of the solution, which is necessary to prevent sedimentation of the suspended particles and thus aggregation or caking of the particles. Example of suspending agents are cellulose derivatives (CMC, HPMC, HEC), carbomers (carbopol, polycarophil), gums, alginates, gelatin, or colloidal silicon dioxide.

Emulsifying agents: An emulsifying agent helps maintain the dispersion of finely divided liquid droplets in a liquid vehicle. Emulsions are made of two or more immiscible liquids such as water and an oil, and can be a liquid or a semisolid such as a cream or lotion. The emulsifying agents can be of natural origin like the lecithins (phospholipids) or synthetic such as ionic (SLS) or non-ionic surfactants (cremophors, polysorbates, poloxamers).

Solubilizing agents: A solubilizing agent is used to enhance the solubility and increase the bioavailability of a sparingly soluble drug. Solubilizing agents can be water-miscible alcoholic solvents like (polyethyleneglycol, propyleneglycol, glycerol), complexing agents such as the cyclodextrins or water-soluble synthetic polymers like povidone (PVP) or polyvinylalcohol (PVA).

Thickening agents: A thickening agent is added to increase the viscosity of the suspension. All the ingredients are mixed by mechanical shaking to get a stable an homogeneous dispersion/suspension/solution of the active lipogenesis and lipid secretion enhancing thiol-containing, —SeH containing, or disulfide-containing drug or pharmaceutical agent in the ointment or gel with the aid of the suspending, solubilizing, emulsifying or thickening agents.

The pharmaceutical compositions described herein comprise from about 0.2% to about 10% lipogenesis and lipid secretion enhancing thiol-containing, —SeH containing, or disulfide-containing drug or pharmaceutical agent. In some embodiments, the pharmaceutical compositions described herein comprise from about 0.2% to about 1.0% lipogenesis and lipid secretion enhancing thiol-containing, —SeH containing, or disulfide-containing drug or pharmaceutical agent. In some embodiments, the pharmaceutical compositions described herein comprise from about 1.0% to about 3.0% lipogenesis and lipid secretion enhancing thiol-containing, —SeH containing, or disulfide-containing drug or pharmaceutical agent. In some embodiments, the pharmaceutical compositions described herein comprise from about 3.0% to about 5.0% lipogenesis and lipid secretion enhancing thiol-containing, —SeH containing, or disulfide-containing drug or pharmaceutical agent. In some embodiments, the pharmaceutical compositions described herein comprise from about 5.0% to about 10.0% lipogenesis and lipid secretion enhancing thiol-containing, —SeH containing, or disulfide-containing drug or pharmaceutical agent. In some embodiments, the pharmaceutical compositions described herein comprise from about 1.0% lipogenesis and lipid secretion enhancing thiol-containing, —SeH containing, or disulfide-containing drug or pharmaceutical agent. In some embodiments, the pharmaceutical compositions described herein comprise from about 1.5% lipogenesis and lipid secretion enhancing thiol-containing, —SeH containing, or disulfide-containing drug or pharmaceutical agent. In some embodiments, the pharmaceutical compositions described herein comprise from about 2.0% lipogenesis and lipid secretion enhancing thiol-containing, —SeH containing, or disulfide-containing drug or pharmaceutical agent. In some embodiments, the pharmaceutical compositions described herein comprise from about 2.5% lipogenesis and lipid secretion enhancing thiol-containing, —SeH containing, or disulfide-containing drug or pharmaceutical agent. In some embodiments, the pharmaceutical compositions described herein comprise from about 3.0% lipogenesis and lipid secretion enhancing thiol-containing, —SeH containing, or disulfide-containing drug or pharmaceutical agent. In some embodiments, the pharmaceutical compositions described herein comprise from about 3.5% lipogenesis and lipid secretion enhancing thiol-containing, —SeH containing, or disulfide-containing drug or pharmaceutical agent. In some embodiments, the pharmaceutical compositions described herein comprise from about 4.0% lipogenesis and lipid secretion enhancing thiol-containing, —SeH containing, or disulfide-containing drug or pharmaceutical agent. In some embodiments, the pharmaceutical compositions described herein comprise from about 4.5% lipogenesis and lipid secretion enhancing thiol-containing, —SeH containing, or disulfide-containing drug or pharmaceutical agent. In some embodiments, the pharmaceutical compositions described herein comprise from about 5.0% lipogenesis and lipid secretion enhancing thiol-containing, —SeH containing, or disulfide-containing drug or pharmaceutical agent.

One embodiment provides a method for treating meibomian gland dysfunction in a patient in need thereof by topical administration of a composition comprising at least one lipogenesis and lipid secretion enhancing thiol-containing, —SeH containing, or disulfide-containing drug or pharmaceutical agent, wherein the lipogenesis and lipid secretion enhancing thiol-containing, —SeH containing, or disulfide-containing drug or pharmaceutical agent results in a therapeutically-relevant increase in the quantity of lipids secreted from the meibomian gland. Another embodiment provides a method for treating meibomian gland dysfunction in a patient in need thereof by topical administration of a composition comprising a lipogenesis and lipid secretion enhancing thiol-containing, —SeH containing, or disulfide-containing drug or pharmaceutical agent, wherein the lipogenesis and lipid secretion enhancing pharmaceutical agent is a pharmaceutical composition comprising selenium sulfide. Another embodiment provides a method for treating meibomian gland dysfunction in a patient in need thereof by topical administration of a composition comprising a lipogenesis and lipid secretion enhancing pharmaceutical agent, wherein the lipogenesis and lipid secretion enhancing pharmaceutical agent is a pharmaceutical composition comprising a thiol-containing, —SeH containing, or disulfide-containing drug. Another embodiment provides a method for treating meibomian gland dysfunction in a patient in need thereof by topical administration of a composition comprising a lipogenesis and lipid secretion enhancing thiol-containing, —SeH containing, or disulfide-containing drug or pharmaceutical agent, wherein the lipogenesis and lipid secretion enhancing thiol-containing, —SeH containing, or disulfide-containing drug or pharmaceutical agent causes increased meibum production. Another embodiment provides a method for treating meibomian gland dysfunction in a patient in need thereof by topical administration of a composition comprising a lipogenesis and lipid secretion enhancing thiol-containing, —SeH containing, or disulfide-containing drug or pharmaceutical agent, wherein the lipogenesis and lipid secretion enhancing thiol-containing, —SeH containing, or disulfide-containing drug or pharmaceutical agent is a Pemphigus causing agent. Another embodiment provides a method for treating meibomian gland dysfunction in a patient in need thereof by topical administration of a composition comprising a lipogenesis and lipid secretion enhancing thiol-containing, —SeH containing, or disulfide-containing drug or pharmaceutical agent, wherein the lipogenesis and lipid secretion enhancing pharmaceutical agent is capable of increasing the quantity of meibum lipids secreted from the meibomian gland and altering the meibum lipids composition, thereby allowing dissolution of meibomian gland obstruction. Another embodiment provides a method for treating meibomian gland dysfunction in a patient in need thereof by topical administration of a composition comprising a lipogenesis and lipid secretion enhancing thiol-containing, —SeH containing, or disulfide-containing drug or pharmaceutical agent, wherein the lipogenesis and lipid secretion enhancing thiol-containing, —SeH containing, or disulfide-containing drug or pharmaceutical agent is capable of increasing the quantity of meibum lipids secreted from the meibomian gland upon application to eyelid margins, by virtue of its contact with the contents of the meibomian gland orifice.

One embodiment provides a method for treating meibomian gland dysfunction by topical administration of a composition comprising a lipogenesis and lipid secretion enhancing thiol-containing, —SeH containing, or disulfide-containing drug or pharmaceutical agent, wherein the lipogenesis and lipid secretion enhancing pharmaceutical agent is a pharmaceutical composition wherein at least one agent is capable of increasing the quantity of meibum lipids secreted from the meibomian gland. Another embodiment provides a method for treating meibomian gland dysfunction in a patient in need thereof by topical administration of a composition comprising a lipogenesis and lipid secretion enhancing pharmaceutical agent, wherein the lipogenesis and lipid secretion enhancing pharmaceutical agent is a pharmaceutical composition comprising selenium sulfide. Another embodiment provides a method for treating meibomian gland dysfunction by topical administration of a composition comprising a lipogenesis and lipid secretion enhancing pharmaceutical agent, wherein the lipogenesis and lipid secretion enhancing pharmaceutical agent is a pharmaceutical composition wherein the at least one agent capable of increasing the quantity of meibum lipids secreted from the meibomian gland is a thiol-containing, —SeH containing, or disulfide-containing drug. Another embodiment provides a method for treating meibomian gland dysfunction by topical administration of a composition comprising a lipogenesis and lipid secretion enhancing thiol-containing, —SeH containing, or disulfide-containing drug or pharmaceutical agent, wherein the lipogenesis and lipid secretion enhancing thiol-containing, —SeH containing, or disulfide-containing drug or pharmaceutical agent is a pharmaceutical composition wherein the at least one agent capable of increasing the quantity of meibum lipids secreted from the meibomian gland causes sebum over-production. Another embodiment provides a method for treating meibomian gland dysfunction by topical administration of a composition comprising a lipogenesis and lipid secretion enhancing thiol-containing, —SeH containing, or disulfide-containing drug or pharmaceutical agent, wherein the lipogenesis and lipid secretion enhancing thiol-containing, —SeH containing, or disulfide-containing drug or pharmaceutical agent is a pharmaceutical composition wherein the at least one agent capable of increasing the quantity of meibum lipids secreted from the meibomian gland is a Pemphigus causing agent. Another embodiment provides a method for treating meibomian gland dysfunction by topical administration of a composition comprising a lipogenesis and lipid secretion enhancing thiol-containing, —SeH containing, or disulfide-containing drug or pharmaceutical agent, wherein the lipogenesis and lipid secretion enhancing thiol-containing, —SeH containing, or disulfide-containing drug or pharmaceutical agent is a pharmaceutical composition wherein the at least one agent capable of increasing the quantity of meibum lipids secreted from the meibomian gland lowers the melting point of meibum lipids, thereby reducing the viscosity of meibum lipids and allowing dissolution of any meibomian gland obstruction. Another embodiment provides a method for treating meibomian gland dysfunction by topical administration of a composition comprising a lipogenesis and lipid secretion enhancing thiol-containing, —SeH containing, or disulfide-containing drug or pharmaceutical agent, wherein the lipogenesis and lipid secretion enhancing thiol-containing, —SeH containing, or disulfide-containing drug or pharmaceutical agent is a pharmaceutical composition wherein at least one agent is capable of increasing the quantity of meibum lipids secreted from the meibomian gland upon application to eyelid margins, by virtue of its contact with the contents of the meibomian gland orifice.

One embodiment provides a method for treating meibomian gland dysfunction by topical administration of a composition comprising a lipogenesis and lipid secretion enhancing pharmaceutical agent, wherein the lipogenesis and lipid secretion enhancing pharmaceutical agent is a drug containing a thiol or disulfide group. Another embodiment provides a method for treating meibomian gland dysfunction by topical administration of a composition comprising a lipogenesis and lipid secretion enhancing pharmaceutical agent, wherein the thiol containing drug is selected from the group consisting of Captopril, Zofenopril, Tiopronin, Penicillamine, L-Cysteine, Selenocysteine, Gluthatione, Dithiothreitol, Thiorphan, Cysteamine, Bucillamine, Dimercaprol, 1,1-Ethanedithiol, Dimercaptosuccinic acid, Furan-2-ylmethanethiol, Omapatrilat, Ovothiol A, Pantetheine, Rentiapril, Thiosalicylic acid, Tixocortol, Mycothiol, Coenzyme A, and Coenzyme B.

Another embodiment provides a method for treating meibomian gland dysfunction by topical administration of a composition comprising a lipogenesis and lipid secretion enhancing pharmaceutical agent, wherein the disulfide containing drug is selected from the group consisting of disulfiram, Psammaplin A, Dixanthogen, Pantethine, Fursultiamine, Octotiamine, Sulbutiamine, Prosultiamine, Thiram, Lipoic acid, Lenthionine, Ajoene, Allicin, Gemopatrilat, and Sulfanegen.

In any of the aforementioned embodiments, the composition further comprises an ophthalmically-acceptable carrier. In one further embodiment, the ophthalmically-acceptable carrier comprises an ophthalmically-acceptable excipient.

In certain embodiments, lipogenesis and lipid secretion enhancing thiol-containing, —SeH containing, or disulfide-containing drug or pharmaceutical agents used in the methods and compositions described herein are optionally used in a maintenance therapy setting. In certain embodiments, lipogenesis and lipid secretion enhancing thiol-containing, —SeH containing, or disulfide-containing drug or pharmaceutical agents used in a maintenance therapy setting include low concentrations of a lipogenesis and lipid secretion enhancing pharmaceutical agent.

The term "maintenance therapy" or "maintenance dosing regime" refers to a treatment schedule for a subject or patient diagnosed with a disorder/disease, e.g., MGD, to enable them to maintain their health in a given state, e.g., remission.

In one embodiment, the lipogenesis and lipid secretion enhancing thiol-containing, —SeH containing, drug or pharmaceutical agent used in maintenance therapy setting is selected from the group consisting of Captopril, Zofenopril, Tiopronin, Penicillamine, L-Cysteine, Selenocysteine, Gluthatione, Dithiothreitol, Thiorphan, Cysteamine, Bucillamine, Dimercaprol, 1,1-Ethanedithiol, Dimercaptosuccinic acid, Furan-2-ylmethanethiol, Omapatrilat, Ovothiol A, Pantetheine, Rentiapril, Thiosalicylic acid, Tixocortol, Mycothiol, Coenzyme A, and Coenzyme B.

In one embodiment, the lipogenesis and lipid secretion enhancing disulfide-containing drug or pharmaceutical agent used in maintenance therapy setting is selected from the group consisting of disulfiram, Psammaplin A, Dixanthogen, Pantethine, Fursultiamine, Octotiamine, Sulbutiamine, Prosultiamine, Thiram, Lipoic acid, Lenthionine, Ajoene, Allicin, Gemopatrilat, and Sulfanegen.

One embodiment provides a method for enhancing lipogenesis and lipid secretion, from meibomian gland, in a patient in need thereof by administering a topical composition comprising a lipogenesis and lipid secretion enhancing thiol-containing, —SeH containing, or disulfide-containing drug or pharmaceutical agent, wherein the composition comprises 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.5%, 5%, or 10% of lipogenesis and lipid secretion enhancing thiol-containing, —SeH containing, or disulfide-containing drug or pharmaceutical agent. In some embodiments, the composition is formulated as a suspension, emulsion, cream, lotion, gel, or ointment. In some embodiments, the composition is applied as a thin layer to clean skin initially once daily on alternate days, and is then gradually increased up to twice daily as tolerance develops. In some embodiments, the composition is an ointment or paste. In some embodiments, the composition is started as a 0.1% ointment. After 7 days, the concentration may be increased to 0.25% and subsequently doubled, if necessary, at weekly intervals to a maximum strength of 2%. In some embodiments, a thin layer of ointment is applied once daily to the affected areas for 2-4 weeks. In some embodiments, the ointment is left in place for 10 to 20 minutes before the area is rinsed thoroughly. In some embodiments, the concentration of lipogenesis and lipid secretion enhancing thiol-containing, —SeH containing, or disulfide-containing drug or pharmaceutical agent is gradually increased to a maximum of 5%, and treatment is continued for as long as necessary.

In other embodiments, the topical compositions described herein are combined with a pharmaceutically suitable or acceptable carrier (e.g., a pharmaceutically suitable (or acceptable) excipient, physiologically suitable (or acceptable) excipient, or physiologically suitable (or acceptable) carrier). Exemplary excipients are described, for example, in *Remington: The Science and Practice of Pharmacy* (Gennaro, 21$^{st}$ Ed. Mack Pub. Co., Easton, Pa. (2005)).

One embodiment provides a method for treating meibomian gland dysfunction by administering a topical composition comprising a lipogenesis and lipid secretion enhancing thiol-containing, —SeH containing, or disulfide-containing drug or pharmaceutical agent. One embodiment provides a method for treating meibomian gland dysfunction by administering a topical composition comprising a lipogenesis and lipid secretion enhancing thiol-containing, —SeH containing, or disulfide-containing drug or pharmaceutical agent combined with a keratolytic agent.

In some embodiments, the topical administration of the composition comprising a lipogenesis and lipid secretion enhancing thiol-containing, —SeH containing, or disulfide-containing drug or pharmaceutical agent occurs once a week. In some embodiments, the topical administration of the composition comprising a lipogenesis and lipid secretion enhancing thiol-containing, —SeH containing, or disulfide-containing drug or pharmaceutical agent occurs twice a week. In some embodiments, the topical administration of the composition comprising a lipogenesis and lipid secretion enhancing thiol-containing, —SeH containing, or disulfide-containing drug or pharmaceutical agent occurs every other day. In some embodiments, the topical administration of the composition comprising a lipogenesis and lipid secretion enhancing thiol-containing, —SeH containing, or disulfide-containing drug or pharmaceutical agent occurs every day. In some embodiments, the topical administration of the composition comprising a lipogenesis and lipid secretion enhancing thiol-containing, —SeH containing, or disulfide-containing drug or pharmaceutical agent occurs several times a day.

In some embodiment, the method comprises treatment in an acute treatment scenario. In another embodiment, the method comprises treatment of a patient naïve to similar or identical treatment. In another embodiment, the method comprises treatment in a chronic treatment scenario. In another embodiment, the method comprises treatment in a maintenance therapy scenario. In an acute treatment scenario, the administered dosage of lipogenesis and lipid secretion enhancing thiol-containing, —SeH containing, or disulfide-containing drug or pharmaceutical agent may be higher than the administered dosage of lipogenesis and lipid secretion enhancing thiol-containing, —SeH containing, or disulfide-containing drug or pharmaceutical agent employed in a chronic treatment scenario or a maintenance therapy scenario. In an acute treatment scenario, the lipogenesis and lipid secretion enhancing thiol-containing, —SeH containing, or disulfide-containing drug or pharmaceutical agent may be different from the lipogenesis and lipid secretion thiol-containing, —SeH containing, or disulfide-containing drug or enhancing pharmaceutical agent employed in a chronic treatment scenario. In some embodiments, the course of therapy begins in the initial phase of therapy as an acute treatment scenario and later transitions into a chronic treatment scenario or a maintenance therapy scenario.

In certain clinical presentations, patients may require an initial treatment administered by a physician or healthcare professional, either by placing a more highly concentrated composition of one of the therapeutic agents described herein. In the event the higher concentration compositions are required, the application thereof may require ocular shielding or other activity to minimize the impact of irritation or disruption of the ocular surface or surrounding tissues. Following such a procedure, a patient may be given a different composition of active agent to take home to apply periodically to the lid margin to maintain the patency of the meibomian gland. Such application may occur twice daily, once a day, weekly or monthly, depending on the composition activity and the desired product profile of the therapy.

One aspect of the methods of treatment described herein is the location of the topical administration of the composition. In one embodiment, the composition comprising a lipogenesis and lipid secretion enhancing thiol-containing, —SeH containing, or disulfide-containing drug or pharmaceutical agent is administered such that no irritation to eye occurs. In one embodiment, the composition comprising a lipogenesis and lipid secretion enhancing thiol-containing, —SeH containing, or disulfide-containing drug or pharmaceutical agent is administered to the eye lid margin.

One additional embodiment of the methods of treatment described herein is the use of a protective element provided to the eye to avoid irritation to the eye. Although the compositions described herein are generally non-irritating, in some embodiments (e.g., high concentration of agent or when used on a sensitive eye) a protective element provides an additional layer of safety and comfort for the patient. In one embodiment, the composition comprising a lipogenesis and lipid secretion enhancing thiol-containing, —SeH containing, or disulfide-containing drug or pharmaceutical agent is administered while an eye shield is placed on the eye to reduce contact of the agent with the cornea and/or conjunctiva such that reduced irritation to eye occurs. In some embodiments, the eye shield is a contact lens or an eye covering. In some embodiments, the eye covering comprises a self-adhesive. In one embodiment, the composition comprising a lipogenesis and lipid secretion enhancing thiol-containing, —SeH containing, or disulfide-containing drug or pharmaceutical agent is administered while the lid is pulled away from the globe to reduce contact of the agent with the cornea and/or conjunctiva such that reduced irritation to eye occurs.

As used herein, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and sub-combinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

The term "ophthalmically-acceptable carrier" as used herein refers to a carrier that does not cause significant irritation to the eye of an organism when applied in accordance with the teachings of the present invention and does not abrogate the pharmacological activity and properties of an agent carried therewith.

Ophthalmically acceptable carriers are generally sterile, essentially free of foreign particles, and generally have a pH in the range of 5-8. Preferably, the pH is as close to the pH of tear fluid (7.4) as possible. Ophthalmically acceptable carriers are, for example, sterile isotonic solutions such as isotonic sodium chloride or boric acid solutions. Such carriers are typically aqueous solutions contain sodium chloride or boric acid. Also useful are phosphate buffered saline (PBS) solutions.

The term "effective amount" as used herein refers to the amount that is needed to achieve a particular condition, such as increasing lipid secretion from a meibomian gland, lowering the melting point of lipids secreted from a meibomian gland or reducing the viscosity of lipids secreted from a meibomian gland.

The term "therapeutically effective amount" as used herein refers to an amount of a therapeutically effective compound, or a pharmaceutically acceptable salt thereof, which is effective to treat, prevent, alleviate or ameliorate symptoms of a disease. The term "therapeutically effective compound" refers to a compound that is effective to treat, prevent, alleviate or ameliorate symptoms of a disease.

The term "sulfhydryl group" as used herein refers to the —SH functional group.

The term "thiol group" as used herein refers to —C—SH or R—SH group, where R represents an alkane, alkene, or other carbon-containing group of atoms.

The term "disulfide" as used herein refers to a linked pair of sulfur atoms.

The term "disulfide bond" as used herein refers to a covalent bond, usually derived by the coupling of two thiol groups, the overall connectivity is therefore —S—S—. The linkage is also called an SS-bond or disulfide bridge.

The term "ophthalmically-acceptable excipient" as used herein refers to an excipient that does not cause significant irritation to the eye of an organism when applied in accordance with the teachings of the present invention and does not abrogate the pharmacological activity and properties of an agent carried therewith.

The term "keratolytic agent" as used herein refers to a compound which loosens and removes the stratum corneum of the skin, or alters the structure of the keratin layers of skin.

The terms "treat," "treating," or "treatment" as used herein, include reducing, alleviating, abating, ameliorating, relieving, or lessening the symptoms associated with MGD in either a chronic or acute therapeutic scenario. In one embodiment, treatment includes an increase in lipid production. In one embodiment, treatment includes an increase in lipid secretion. In one embodiment, treatment includes a decrease in the viscosity of the lipids secreted.

The term "recurrence," or "reducing relapse" refers to return of MGD symptoms in a chronic therapeutic scenario.

The term "opening" refers to the clearing (at least in part) of an obstructed meibomian gland canal or orifice and/or maintaining the patency of the meibomian gland canal or orifice.

The term "lipogenesis and lipid secretion enhancing thiol-containing, —SeH containing, or disulfide-containing drug or pharmaceutical agent" as used herein refer to a thiol-containing, —SeH containing, or disulfide-containing drug or pharmaceutical agent that causes increases differentiation of meibocytes or increases proliferation of meibocytes or increases the quantity of lipids secreted from the meibomian glands or alters the composition of meibum lipids.

The term "meibum lipids" as used herein refers to lipids secreted by meibomian gland.

The term "lotion" describes an emulsion liquid dosage form. This dosage form is generally for external application to the skin (US FDA Drug Nomenclature Monograph, number C-DRG-00201).

The term "cream" describes an emulsion semisolid dosage form, usually containing >20% water and volatiles and/or <50% hydrocarbons, waxes or polyols as the vehicle. A cream is more viscous than a lotion. This dosage form is generally for external application to the skin (US FDA Drug Nomenclature Monograph, number C-DRG-00201).

The term "ointment" describes a semisolid dosage form, usually containing <20% water and volatiles and/or >50% hydrocarbons, waxes or polyols as the vehicle. This dosage form is generally for external application to the skin or mucous membranes (US FDA Drug Nomenclature Monograph, number C-DRG-00201).

The term "solution" describes a clear, homogeneous liquid dosage form that contains one or more chemical substances dissolved in a solvent or mixture of mutually miscible solvents (US FDA Drug Nomenclature Monograph, number C-DRG-00201).

The term "suspension" refers to a heterogeneous mixture containing solid particles that are sufficiently large for sedimentation.

The term "lipid-derivative" as used herein generally refers to hydrophobic or amphiphilic molecules comprising at least one sulfhydryl group or at least one disulfide. The term "lipid-derivative" further refers to hydrophobic or amphiphilic molecules comprising at least one sulfhydryl group and at least one disulfide. The term "lipid-derivative" further refers to combinations and mixtures of lipid-derivatives.

Figure 4:
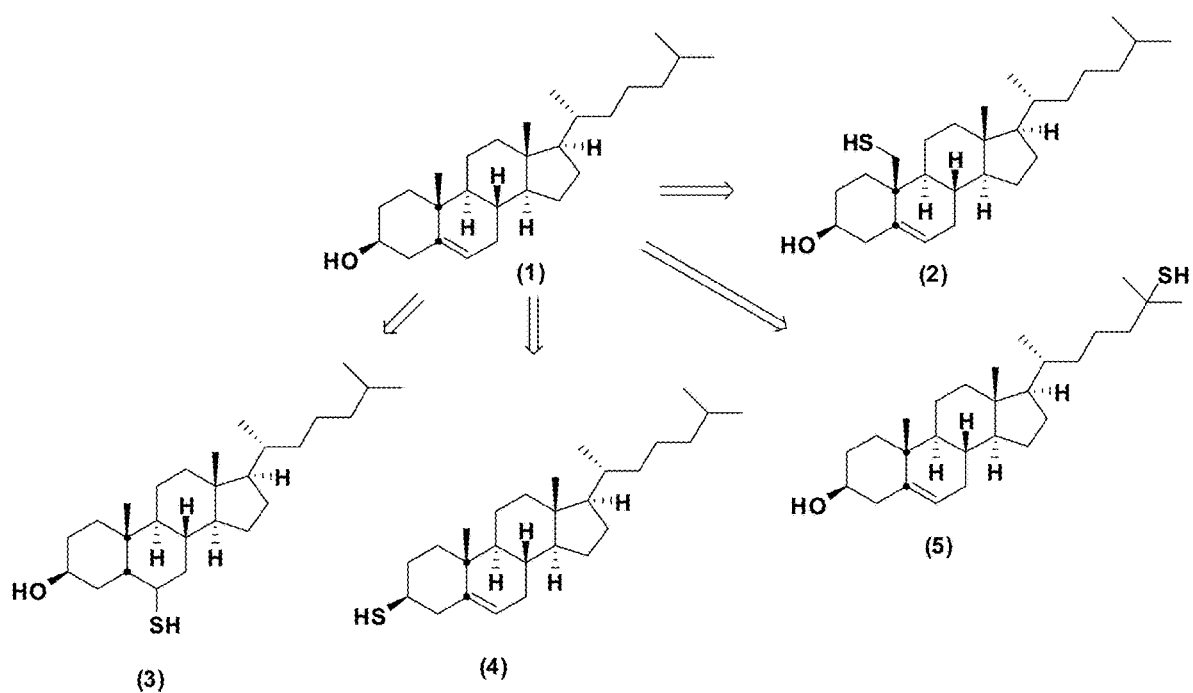
FIG. 4 provides illustrative synthetic methods to prepare the thiol and disulfide-containing lipids employed in the methods described herein.
Figure 5:
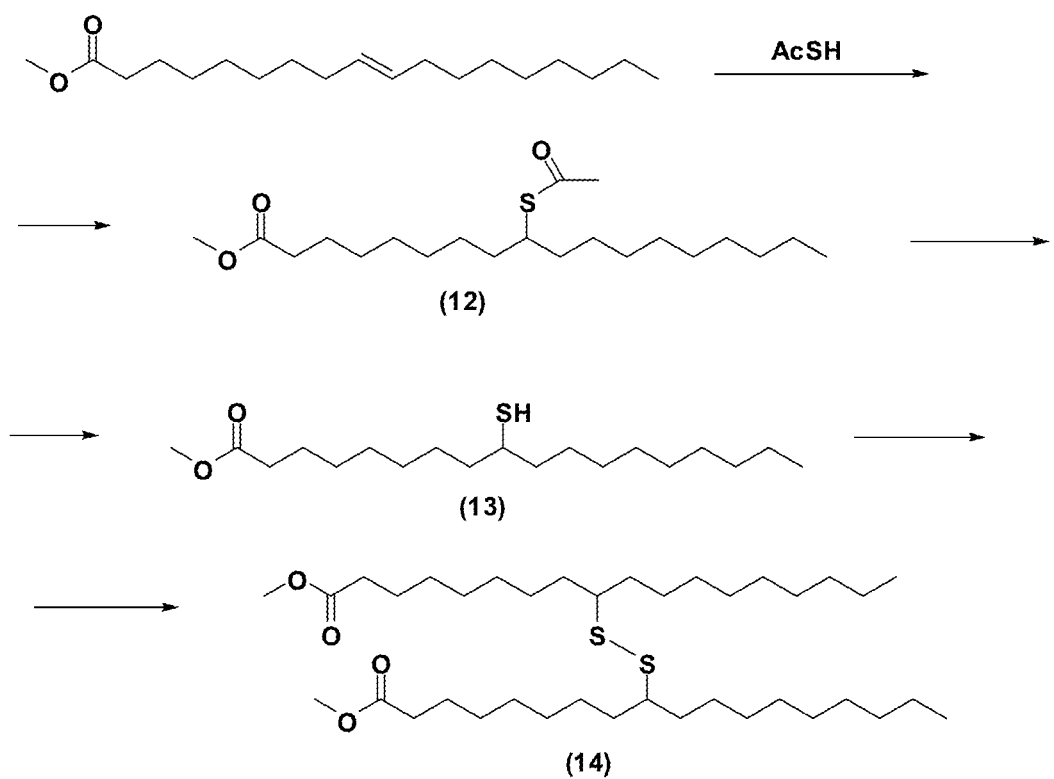
FIG. 5 provides illustrative synthetic methods to prepare the thiol and disulfide-containing lipids employed in the methods described herein.
Figure 6:
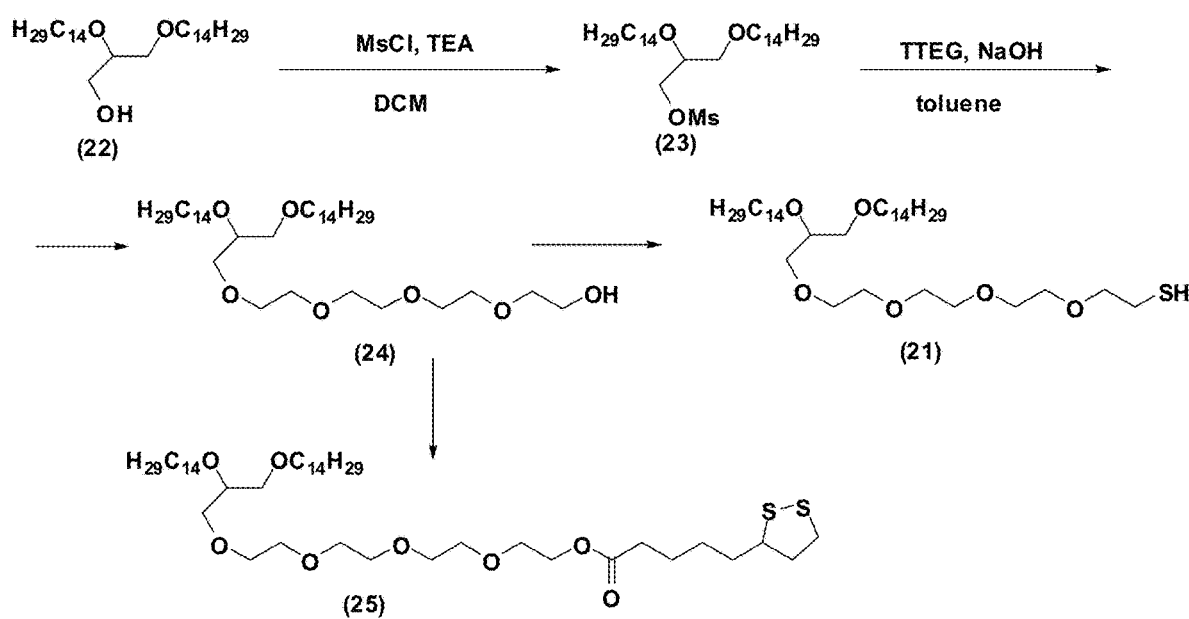
FIG. 6 provides illustrative synthetic methods to prepare the thiol and disulfide-containing lipids employed in the methods described herein.
Figure 7:
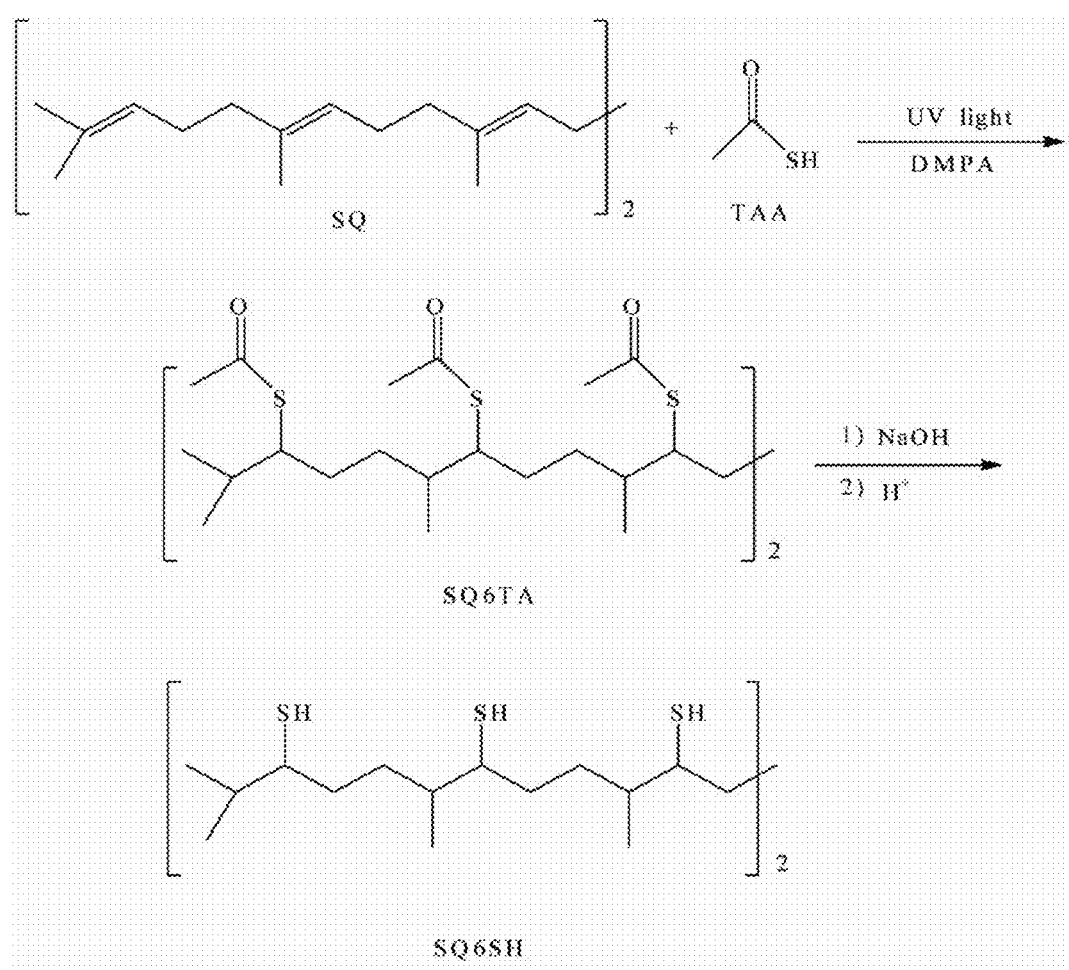
FIG. 7 provides illustrative synthetic methods to prepare the thiol and disulfide-containing lipids employed in the methods described herein.
Figure 8:
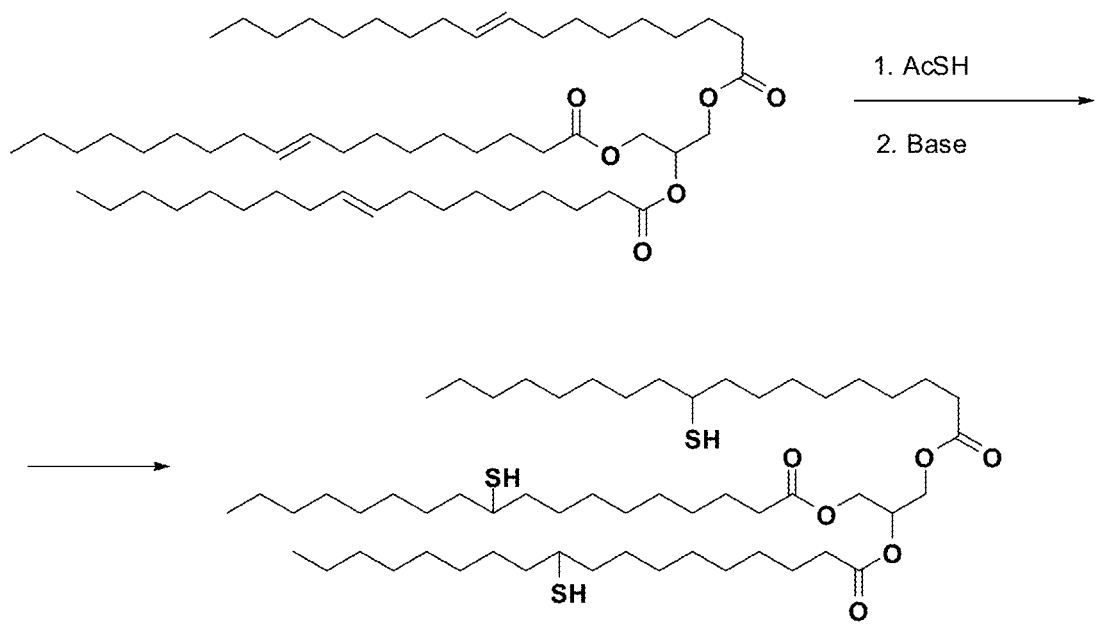
FIG. 8 provides illustrative synthetic methods to prepare the thiol and disulfide-containing lipids employed in the methods described herein.

The thiol-containing and/or disulfide-containing lipids or "lipid-derivatives" described by the present invention are highly heterogeneous in terms of structure and derivation levels. For examples, lipids, such as cholesterol, may have a plurality of different thiol-containing derivatives (FIG. 4). Methods to synthesize fatty thiol compounds were previously described (J. Org. Chem., 1958, Vol. 23, pages 1525-1530), producing a plurality of lipids linked by a disulfide (FIG. 5). Also previously described are methods for synthesizing disulfide-containing lipids (FIG. 6), as well as methods for synthesizing multiple-thiol-containing lipids, such as squalene (FIG. 7). Mono-, di- and tri-glycerides were also converted to their thiol-containing derivatives (FIG. 8). In summary, lipids may be derivative to produce a wide range of thiol-containing and/or disulfide-containing derivatives by methods which are well known in the art.

EXAMPLES

Example 1: In Vivo Evaluation of the Effect of Thiol or Disulfide Containing Compounds on Lipid Synthesis in a 3D Model Culture of Sebocytes Since secretory cells (meibocytes) of meibomian glands, share similarities with that of the secretory cells (sebocytes) of sebaceous glands, as can be validated from their similar structure, similar function and their joint embryologic development (Knop 2011_IOVS) the effect of Thiol containing Lipids on lipid production can be evaluated in a 3D model culture of Sebocytes. See also: Barrault 2012, Immortalized sebocytes can spontaneously differentiate into a sebaceous-like phenotype when cultured as a 3D epithelium, Exp. Derm, 21:299-319

The effect of different compounds on lipid synthesis was evaluated, in a 3D model culture of Sebocytes. Drug candidates were drugs containing S—H or disulfide: Selenium disulfide (SeS2 dispersed in CarboxymethylCellulose—CMC) as a positive control, Selenocysteine, Captopril, Disulfiram and lipids containing S—H or disulfide: Thioethanol, 12-Mercaptododecanoic acid. Since Sebocytes differentiation is associated with increased lipid synthesis and accumulation, evaluation of proliferation and differentiation was done by quantifying lipid accumulation in the 3D Sebocytes culture (human cell line—SEBO662). Lipid accumulation was evaluated by lipid staining with Oil red staining.

Sebocytes SEBO662 were cultured into a three dimension (3D) epithelium and differentiated to a sebaceous-like phenotype. The Sebocytes were treated or not (control) with the test compounds and incubated for 14 days. All experiments were performed 3 times. After incubation, tissues were snap-frozen. Formaldehyde-fixed cryo sections were stained using an Oil-red-O solution and counterstained using haematoxylin. For each test condition, the sections were observed using a light microscope equipped with a camera. Five pictures were taken per replicate, making 15 values per treatment condition. The lipid content in each sample was quantified by calculation of the lipid droplet surface area. Quantitative comparison of all data points between lipid's droplet surface area of tested compounds versus control was performed Results:

FIG. 1 is an illustration of Oil-red-0 staining in 3D Sebocytes epithelium for the control.

Figure 2:
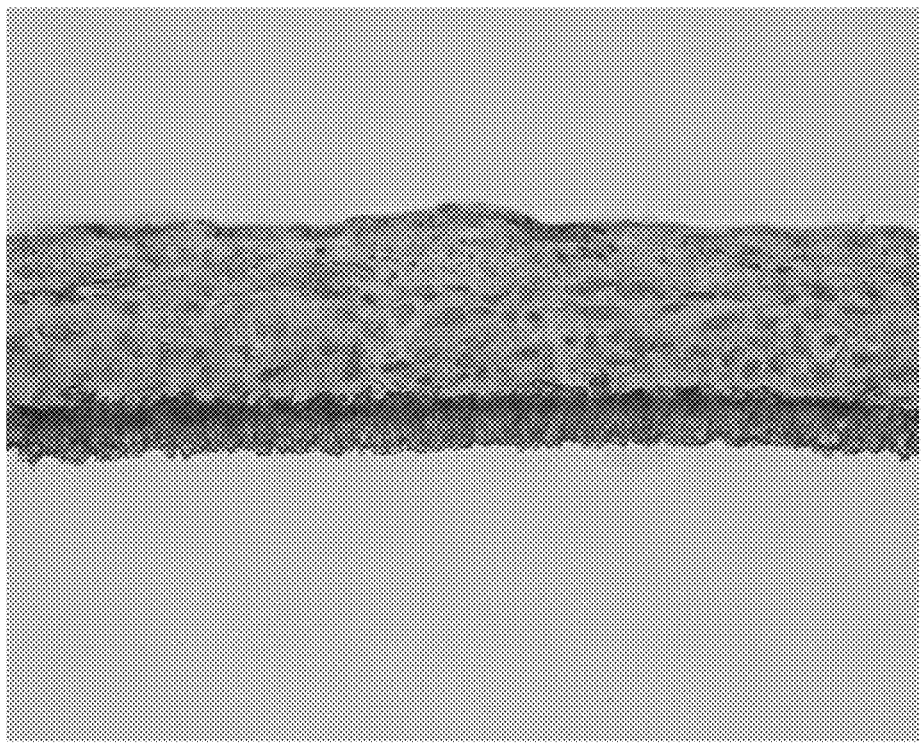
FIG. 2 is an illustration of Oil-red-0 staining in 3D Sebocytes epithelium for 1.0 micromolar 12-mercaptododecanoic acid.

FIG. 2 is an illustration of Oil-red-0 staining in 3D Sebocytes epithelium for 1.0 micromolar 12-mercapto-dodecanoic acid.

Figure 3:
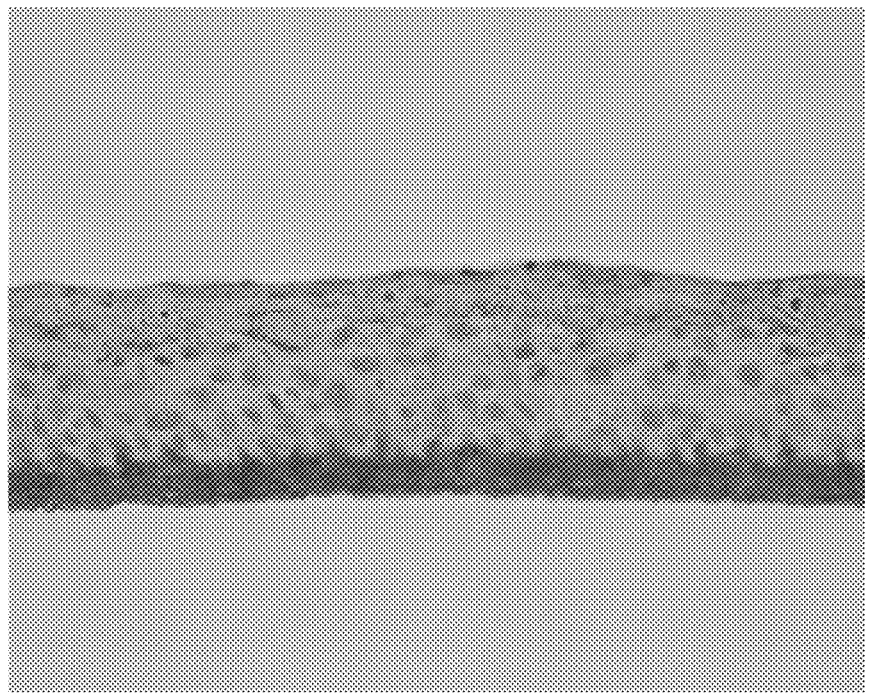
FIG. 3 is an illustration of Oil-red-0 staining in 3D Sebocytes epithelium for 0.1 micromolar 12-mercaptododecanoic acid.

FIG. 3 is an illustration of Oil-red-0 staining in 3D Sebocytes epithelium for 0.1 micromolar 12-mercapto-dodecanoic acid.

Quantitative Comparison

Selenium disulfide (SeS2), at 0.01 µM and 0.1 µM, induced a statistically significant increase of lipid accumulation, in the upper region of the 3D Sebocytes, at both test concentrations (282% and 348% of the control, respectively).

Selenocysteine, tested at 1 µM and 10 µM. At concentration of 1 µM, the compound induced a statistically significant increase in lipid accumulation in the 3D sebocytes (296% of the control). At 10 µM, no stimulation effect was found.

Captopril, tested at 1.0 µM and 10 µM, induced a statistically significant increase of lipid accumulation, at both test concentrations (240% and 173% of the control, respectively).

Disulfiram, tested at 100 µM and 1000 µM. At concentration of 100 µM stimulated a statistically significant increase in lipid accumulation in the 3D sebocytes (199% of the control). At 1000 µM, no stimulation effect was found.

Thioethanol, tested at 0.1 and 1 µM, stimulated a statistically significant increase of lipid accumulation, at both test concentrations (251% and 228% of the control, respectively).

12-Mercaptododecanoic acid, tested at 0.1 µM and 1 µM, induced a statistically significant increase of lipid accumulation in 3D sebocytes. This effect was similar at both concentrations (385% and 349% compared to the control, respectively)

Conclusions:

Selenium disulfide, Selenocysteine, Thioethanol, Captopril, Disulfiram, and 12-Mercaptododecanoic acid, which are compounds that contain S—H or disulfide, had a significant stimulating effect on lipid synthesis in the 3D Sebocytes model.

Example 2: Preparation of a Pharmaceutical Composition Comprising a Lipogenesis and Lipid Secretion Enhancing Thiol-Containing, —SeH Containing, or Disulfide-Containing Drug or Pharmaceutical Agent 2.5 grams of 12-Mercaptododecanoic acid is mixed with 10 grams of liquid paraffin and 87.5 grams of white soft petrolatum and heated to ~60° C. with constant stirring until homogeneous mixture is obtained and cooled to room temperature.

2.5 grams of 12-Mercaptododecanoic acid is mixed with 2.5 grams of cholesterol, 10 grams of liquid petrolatum, and 85 grams of Vaseline. The mixture is heated under mixing until all ingredients melt ~80° C. and homogeneity obtained and then cooled to room temperature.

2.5 grams of 12-Mercaptododecanoic acid is mixed with 5 grams of squalene and 97.5 grams of Vaseline and heated to ~60° C. with mixing in order to obtain homogeneity and then cooled to room temperature 2.5 grams of 12-Mercaptododecanoic acid is mixed with 10 grams of mineral oil, 10 grams of squalene, 10 grams of capric/caprylic triglyceride, 10 grams of microcrystalline wax, 10 grams of hydrogenated vegetable oil, and 3 grams of lanoline and Vaseline to 100 grams. The mixture is heated to ~80° C.-90° C. with mixture until homogeneity is obtained and cooled to room temperature.

2.5 grams of thiocholeterol is mixed with 10 grams of mineral oil, 10 grams of squalene, 10 grams of capric/caprylic triglyceride, 10 grams of microcrystalline wax, 10 grams of hydrogenated vegetable oil, and 3 grams of lanoline and Vaseline to 100 grams. The mixture is heated to ~80° C.-90° C. with mixture until homogeneity is obtained and cooled to room temperature.

2.5 grams of thiophospholipid is mixed with 10 grams of mineral oil, 10 grams of squalene, 10 grams of capric/caprylic triglyceride, 10 grams of microcrystalline wax, 10 grams of hydrogenated vegetable oil, and 3 grams of lanoline and Vaseline to 100 grams. The mixture is heated to ~80° C.-90° C. with mixture until homogeneity is obtained and cooled to room temperature.

2.5 grams of 23-(9-Mercaptononyl)-3,6,9,12,15,18,21-Heptaoxatricosanoic Acid is mixed with 10 grams of mineral oil, 10 grams of squalene, 10 grams of capric/caprylic triglyceride, 10 grams of microcrystalline wax, 10 grams of hydrogenated vegetable oil, and 3 grams of lanoline and Vaseline to 100 grams. The mixture is heated to ~80° C.-90° C. with mixture until homogeneity is obtained and cooled to room temperature.

2.5 grams of disulfiram is mixed with 10 grams of mineral oil, 10 grams of squalene, 10 grams of capric/caprylic triglyceride, 10 grams of microcrystalline wax, 10 grams of hydrogenated vegetable oil, and 3 grams of lanoline and Vaseline to 100 grams. The mixture is heated to ~80° C.-90° C. with mixture until homogeneity is obtained and cooled to room temperature.

2.5 grams of thiophospholipids is mixed with 3 grams of cholesterol and 10 grams of phospholipids and dissolved in ethanol acetone mixture. The mixture is dried under vacuum and mixed with 1000 ml of saline solution under vigorous agitation following high-pressure homogenization to produce very fine liposome dispersion.

2.5 grams of disulfiram is mixed with 5 grams of hydrogenated vegetable oil and 5 grams of mineral oil and heated to ~80° C. with stirring until all ingredients are melted. 87.5 grams of pre heated water solution to 80° C. comprising 1% tween80 and 2% phospholipids are added under vigorous mixing and high shear homogenization. 0.8 grams of xanthan gum (Xantural 3000™) is added under vigorous mixing and the mixture is cooled to room temperature to obtain solid lipid dispersion.

2.5 grams of captopril is dissolved in sterile water for injection, 1.2 grams of xanthan gum and 0.8 grams of sodium chloride are added and the mixture is agitated to produce a clear gel.

Example 3: Increasing Lipid Production in Meibomian Glands

The objective of the study is to evaluate the effect of a lipogenesis and lipid secretion enhancing formulations on increasing the quantity of lipids produced by the meibomian glands.

A light layer of lipogenesis and lipid secretion enhancing thiol-containing, —SeH containing, or disulfide-containing drug or agent is applied to the lower lid of a subject, and the quantity of lipids produced by the meibomian gland is measured before and after application of the drug or agent. An exemplary method to determine the level of lipid production in the meibomian gland is by culturing human meibomian gland epithelial cells with and without the thiol-containing, —SeH containing, or disulfide-containing drug or pharmaceutical agent for 1, 3, 5 and 7 days and then determining the magnitude of cellular lipid and lysosome accumulation by staining cells with LipidTOX green neutral lipid stain and LysoTracker® Red DND-99 (a fluorescent technique designed for labeling lysosomes). Additionally, by examining whether the thiol-containing, —SeH containing, or disulfide-containing drug increases the synthesis of polar and neutral lipid species in human meibomian gland epithelial cells, by culturing cells in media with or without the thiol-containing, —SeH containing, or disulfide-containing drug groups for 7 days and then processing the cells for the identification of phospholipids, and wax and cholesterol esters. These latter 2 species are the predominant lipids in human meibum. The analyses involve the use of highperformance thin-layer chromatography and the quantification of staining intensities with ImageJ dye. Another known alternative method utilizes Oil red O and Nile red staining. The degree of lipid accumulation is determined through the use of Nile Red dye. This dye will give a fluorescent signal which is proportional to the amount of lipids which have been accumulated.

Example 4: Increasing Lipid Secretion from Meibomian Glands

The objective of the study is to evaluate the effect of a lipogenesis and lipid secretion enhancing formulations on increasing the quantity of lipids secreted from the meibomian glands.

A light layer of lipogenesis and lipid secretion enhancing thiol-containing, —SeH containing, or disulfide-containing drug or agent is applied to the lower lid of a subject, and the quantity of lipids secreted from the meibomian gland is measured before and after application of the drug or agent. An exemplary method to determine the level of lipid secretion from the meibomian gland is using a "meibometer" instrument for quantifying meibomian lipid on the lid margin, which is an optical spectrophotometer that has tapes that are put against the lid margin to measure the amount of meibum being secreted (Chew et al, Current Eye Research, Vol. 12 (3), pages 247-254, 1993).

Example 5: Lowering the Melting Point of Lipids Secreted from Meibomian Glands

The objective of the study is to evaluate the effect of a lipogenesis and lipid secretion enhancing formulations on lowering the melting point of lipids secreted from the meibomian glands.

A light layer of lipogenesis and lipid secretion enhancing thiol-containing, —SeH containing, or disulfide-containing drug or agent is applied to the lower lid of a subject, and the melting point of lipids secreted from the meibomian gland is measured before and after application of the drug or agent. An exemplary method to determine the melting point of lipid secretion from the meibomian gland is weighing an amount of 100 milligrams meibum lipids and dissolving them in chloroform-methanol (3:1) solvent mixture. Small portions of the above mixture are withdrawn and put onto a pre-weighed Differential Scanning calorimeter (DSC) pan. Subsequently the solvent is evaporated under a stream of nitrogen to get a uniformly mixed sample. The DSC pans are weighed again to determine the accurate weight of the lipids. The samples are then analyzed in triplicate using the DSC and run from −50° C. to 100° C. at the rate of 5° C./minute. Singular components are also run under similar conditions as reference to identify them in mixtures. The separate components are run as is, as well as after dissolving in chloroform-methanol mixtures and after the evaporation of solvents. The melting points are recorded as peaks in the DSC thermograms.

Example 6: Reducing the Viscosity of Lipids Secreted from Meibomian Glands

The objective of the study is to evaluate the effect of a lipogenesis and lipid secretion enhancing formulations on reducing the viscosity of lipids secreted from the meibomian glands.

A light layer of lipogenesis and lipid secretion enhancing thiol-containing, —SeH containing, or disulfide-containing drug or agent is applied to the lower lid of a subject, and the viscosity of lipids secreted from the meibomian gland is measured before and after application of the drug or agent. An exemplary method to determine the viscosity of lipid secretion from the meibomian gland is by using the Brookfield Cone/Plate Viscometer of special geometry gives researchers a sophisticated instrument for routinely determining absolute viscosity of fluids in small sample volumes. The Brookfield Cone/Plate Viscometer provides a wide variety of shear rates and viscosity ranges, which can be further extended by the use of interchangeable cone spindles. Different models can be selected to meet the specific range of viscosities and shear rates required. The small sample volume required permits rheological evaluations to be made on materials where sample availability is limited, such as biological fluids and meibum samples.

Example 7: Treatment of MGD Patients

The objective of the study is to evaluate the effect of a lipogenesis and lipid secretion enhancing formulations on treating MGD or at least one of its symptoms.

A light layer of lipogenesis and lipid secretion enhancing thiol-containing, —SeH containing, or disulfide-containing drug or agent is applied to the lower lid of an MGD patient, and the severity of MGD or at least one of its symptoms is measured before and after application of the drug or agent. Exemplary methods for assessing and monitoring the severity of MGD or at least one of its symptoms include, but are not limited to patient questionnaires, meibomian gland expression, tear stability break up time, and determining the number of patent glands as seen by digital expression. Other methods for assessing MGD symptoms, include but are not limited to, Shirmer test, ocular surface staining, lid morphology analysis, meibography, meibometry, interferometry, evaporimetry, tear lipid composition analysis, fluorophotometry, meiscometry, osmolarity analysis, indices of tear film dynamics, evaporation and tear turnover.

The invention claimed is:

1. A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is captopril or selenocysteine.

2. The method of claim 1, wherein the ophthalmically-acceptable carrier comprises at least one ophthalmically-acceptable excipient.

3. The method of claim 1, further comprising the step of administering to the patient a keratolytic agent.

4. The method of claim 3, wherein the keratolytic agent is selected from the group consisting of benzoyl peroxide, coal tar, dithranol, salicylic acid, selenium disulfide, alpha-hydroxy acid, urea, boric acid, retinoic acid, lactic acid, sodium thioglycolate or allantoin.

5. A method for increasing lipid secretion from a meibomian gland, comprising topically administering to the eyelid margin of the patient in need thereof an ophthalmic composition comprising an effective amount of a single agent which increases lipogenesis in the meibomian gland or increases lipid secretion from the meibomian gland, wherein the agent is captopril or selenocysteine.

6. The method of claim 5, further comprising the step of administering to the patient a keratolytic agent.

7. The method of claim 6, wherein the keratolytic agent is selected from the group consisting of benzoyl peroxide, coal tar, dithranol, salicylic acid, selenium disulfide, alpha-hydroxy acid, urea, boric acid, retinoic acid, lactic acid, sodium thioglycolate or allantoin.

8. The method of claim 1, wherein the agent is captopril.

9. The method of claim 1, wherein the agent is selenocysteine.

10. The method of claim 5, wherein the agent is captopril.

11. The method of claim 5, wherein the agent is selenocysteine.

* * * * *